US011447811B2

(12) United States Patent
Smith

(10) Patent No.: US 11,447,811 B2
(45) Date of Patent: Sep. 20, 2022

(54) METHOD OF DIAGNOSING A DYSBIOSIS

(71) Applicant: smartDNA Pty Ltd, Clayton (AU)

(72) Inventor: Margaret Smith, Clayton (AU)

(73) Assignee: smartDNA Pty Ltd, Clayton (AU)

( * ) Notice: Subject to any disclaimer, the term of this patent is extended or adjusted under 35 U.S.C. 154(b) by 0 days.

(21) Appl. No.: 16/631,620

(22) PCT Filed: Jul. 17, 2018

(86) PCT No.: PCT/AU2018/050748
§ 371 (c)(1),
(2) Date: Jan. 16, 2020

(87) PCT Pub. No.: WO2019/014714
PCT Pub. Date: Jan. 24, 2019

(65) Prior Publication Data
US 2020/0181674 A1    Jun. 11, 2020

(30) Foreign Application Priority Data

Jul. 17, 2017  (AU) ................................ 2017902786

(51) Int. Cl.
*C12Q 1/06* (2006.01)
*A23L 33/135* (2016.01)
*A61K 35/741* (2015.01)
*C12Q 1/689* (2018.01)

(52) U.S. Cl.
CPC .............. *C12Q 1/06* (2013.01); *A23L 33/135* (2016.08); *A61K 35/741* (2013.01); *C12Q 1/689* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| 2014/0065132 | A1 | 3/2014 | Hsiao et al. |
| 2016/0030494 | A1 | 2/2016 | Henn et al. |
| 2016/0110515 | A1 | 4/2016 | Apte et al. |
| 2017/0035346 | A1 | 2/2017 | Apte et al. |

FOREIGN PATENT DOCUMENTS

| WO | 1998/51693 | | 11/1998 | |
| WO | 2001/53525 | | 7/2001 | |
| WO | 2011/043654 | | 4/2011 | |
| WO | WO-2011043654 | A1 * | 4/2011 | ............... C12Q 1/04 |
| WO | 2012/080754 | | 6/2012 | |
| WO | 2014/138999 | | 9/2014 | |
| WO | 2016/033439 | | 3/2016 | |
| WO | 2016065075 | A1 | 4/2016 | |

OTHER PUBLICATIONS

Caruana & Niculescu-Mizil, (2006) An Empirical Comparison of Supervised Learning Algorithms. Proceedings of the 23 rd International Conference on Machine Learning, Pittsburgh, PA, 8 pages.
Casen, C. et al., "Deviations in human gut microbiota: a novel diagnostic test for determining dysbiosis in patients with IBS or IBD", Alimentary Pharmacology and Therapeutics, 2015, vol. 42, pp. 71-83.
Cole et al., (2007) Nucleic Acids Research. vol. 35—Database issue: D169-D172.
De Angelis, M. et al., "Fecal microbiota and metabolome of children with autism and pervasive developmental disorder not otherwise specified", Plos One 2013, 8(10):e76993.
Dunn, K.A. et al., "Early changes in microbial community structure are associated with sustained remission after nutritional treatment of pediatric Crohn's Disease", Inflammatory Bowel Disease, 2016, vol. 22, pp. 2853-2862.
Durbán, A. et al. 'Structural alterations of faecal and mucosa-associated bacterial communities in irritable bowel syndrome' Environmental Microbiology Reports. 2012, vol. 4, pp. 242-247.
Feng & Doolittle, (1987) Progressive sequence alignment as a prerequisitetto correct phylogenetic trees. J. Mol. Evolution., 25, 351-360.
Finegold, S.M. et al., "Pyrosequencing study of fecal microflora of autistic and control children", Anaerobe, 2010, vol. 16, pp. 444-453.
FLASH: Fast length adjustment of short reads to improve genome assemblies. T. Magoc and S. Salzberg. Bioinformatics 27:21 (2011), 2957-63. https://ccb.jhu.edu/software/FLASH/.
Gevers, D. et al., "The treatment-naive microbiome in new-onset Crohn's Disease", Cell Host and Microbe, 2014, vol. 15, pp. 382-392.
Higgins, H.G. & Sharp, P.M. (1989) Fast and sensitive multiple sequence alignments on a microcomputer. CABIOS, 5:151-153.
Ho, T. K. (1995) Random Decision Forests. Proceedings of the 3rd International Conference on Document Analysis and Recognition, Montreal, QC, Aug. 14-16, 1995 pp. 278-282.
Kang, D-W. et al., "Microbiota Transfer Therapy alters gut ecosystem and improves gastrointestinal and autism symptoms: an open-label study", Microbiome, 2017, 5:10. Published online Jan. 23, 2017.
Knights, D. et al., "Supervised classification of human microbiota", FEMS Microbiology Reviews, 2011, vol. 35, pp. 343-359.
Labus, J.S. et al., "Differences in gut microbial composition correlate with regional brain volumes in irritable bowel syndrome", Microbiome, 2017, 5:49. Published online May 1, 2017.
Needleman, S.B. & Wunsch C.D., (1970) A general method applicable to the search for similarities in the amino acid sequence of two proteins.J. Mol. Biol. 48; 443-453.
Ng, S. C. et al. "Effect of probiotic bacteria on the intestinal microbiota in irritable bowel syndrome" Journal of Gastroenterology and Hepatology (Australia). 2013, vol. 28, pp. 1624-1631.
Ondov, B. D. et al., (2011) "Interactive metagenomic visualization in a Web browser". BMC Bioinformatics. 12:385. doi: 10.1186/1471-2105-12-385.

(Continued)

*Primary Examiner* — Mary Maille Lyons
(74) *Attorney, Agent, or Firm* — Meunier Carlin & Curfman LLC

(57) ABSTRACT

The present disclosure relates to methods of diagnosing a dysbiosis in a subject, methods of determining a suitable treatment, and methods of treating a dysbiosis. In some aspects, the present disclosure relates to diagnosing or determining a subtype of irritable bowel syndrome (IBS).

13 Claims, 3 Drawing Sheets

(56) References Cited

OTHER PUBLICATIONS

Papa, E. et al., "Non-invasive mapping of the gastrointestinal microbiota identifies children with inflammatory bowel disease", Plos One, 2012, 7(6):e39242.

Pruesse, Elmar, et al. "SILVA: a comprehensive online resource for quality checked and aligned ribosomal RNA sequence data compatible with ARB." Nucleic acids research 35.21 (2007): 7188-7196.

Rajilic-Stojanovic, M. et al. 'Global and Deep Molecular Analysis of Microbiota Signatures in Fecal Samples from Patients with Irritable Bowel Syndrome' Gastroenterology. 2011, vol. 141, pp. 1792-1801.

Rasmussen, C. E. & Williams, C. K. I. (2006) Gaussian Processes for Machine Learning. The MIT Press. 266 pages.

Ritari, Jarmo, et al. "Improved taxonomic assignment of human intestinal 16S rRNA sequences by a dedicated reference database." BMC genomics 16.1 (2015): 1056.

Ritchie, Matthew E., et al. "limma powers differential expression analyses for RNA-sequencing and microarray studies." Nucleic acids research 43.7 (2015): e47-e47.

Roig, M. G. (1985) Immobilized Cells and Enzymes: A Practical Approach. IRL Press, Oxford. Description 1 page.

Tap, J. et al., "Identification of an intestinal microbiota signature associated with severity of irritable bowel syndrome", Gastroenterology, 2017, vol. 152, pp. 111-123.

Wang, F. et al., "Detecting microbial dysbiosis associated with pediatric Crohn disease despite the high variability of the gut microbiota", Cell Reports, 2016, vol. 14, pp. 945-955.

Wiedmann, M. et al. "Ligase chain reaction (LCR)-overview and applications." PCR Methods Appl 3.4 (1994): S51-64.

Young, et al., "Efficient isolation of genes by using antibody probes." Proceedings of the National Academy of Sciences 80.5 (1983): 1194-1198.

International Search Report and Written Opinion, issued for Application No. PCT/US2018/050748, dated Sep. 21, 2018.

International Search Report issued by Australian Patent Office, for Application No. AU2017902786, dated Sep. 6, 2017.

European Search Report issued in related European Application No. 18835137.3 dated Jul. 8, 2021.

Written Opinion issued in related Singapore Application No. 11201913701V, dated Nov. 11, 2021.

Rigsbee, L, et al., "Quantitative Profiling of Gut Microbiota of Children with Diarrhea-Predominant Irritable Bowel Syndrome", The American Journal of Gastroenterology (2012) 107 (11), 1740-1751.

Strati, F. et al., "New Evidences on the Altered Gut Microbiota in Autism Spectrum Disorders", Microbiome (2017) 5, 24.

* cited by examiner

METHOD OF DIAGNOSING A DYSBIOSIS

TECHNICAL FIELD

The present disclosure relates to methods of diagnosing a dysbiosis in a subject, methods of determining a suitable treatment, and methods of treating a dysbiosis.

BACKGROUND

The human microbiota consists of several trillion microorganisms, most of which are of bacterial origin and are non-pathogenic. The microbiota plays a crucial role in human health and functions jointly with the host's immune system to protect against the invasion and colonisation of pathogens. It also has an essential metabolic function by providing a source of essential vitamins and nutrients as well as assisting in the extraction of energy and nutrients from food, such as amino acids and short-chain fatty acids. In this regard, the host is highly dependent on its microbiota for a number of critical biological functions, which significantly contribute to health.

There is a growing body of evidence to suggest that dysbiosis of the human microbiota is associated with a number of diseases. However, it is difficult to determine or predict the exact impact that the microbiota has on human health and its involvement in human disease, due to the highly complex interplay between bacterial species in the microbiota. Thus, there is a need for methods that can effectively diagnose a dysbiosis in order to identify subjects at risk of developing associated diseases.

SUMMARY

The present inventors have developed a method of diagnosing a dysbiosis in a subject which involves analysing the microbiome of the subject and comparing it to a reference sample. Additionally, the inventors have identified that there are several bacterial species and genera whose abundance in the microbiome is informative of dysbioses, and subtypes thereof, that are associated with a particular disease, including IBS, autism, and intestinal senescence.

Accordingly, the present disclosure provides a method of determining a subtype of IBS in a subject, comprising determining the abundance of at least 10 genera of bacteria in a sample from the subject or the subject's environment, wherein the at least 10 genera are selected from *Alkaliphilus, Sphingomonas, Pelotomaculum, Eggerthella, Eubacterium, Paracoccus, Lachnoclostridium, Bacillus, Anaerorhabdus, Actinomyces, Methylobacterium, Pseudomonas, Streptococcus, Staphylococcus, Peptoclostridium, Erysipelatoclostridium, Anaerostipes, Sutterella, Brevundimonas, Clostridium, Peptostreptococcaceae, Slackia, Blastomonas, Lactobacillus, Klebsiella, Agrobacterium,* and *Phyllobacterium*.

In one embodiment, the at least 10 genera of bacteria include at least 5 genera selected from *Alkaliphilus, Sphingomonas, Pelotomaculum, Eggerthella, Eubacterium, Paracoccus, Lachnoclostridium, Bacillus, Anaerorhabdus,* and *Actinomyces*.

In one embodiment, the at least 10 genera of bacteria include *Alkaliphilus, Sphingomonas, Pelotomaculum, Eggerthella, Eubacterium, Paracoccus, Lachnoclostridium, Bacillus, Anaerorhabdus,* and *Actinomyces*.

In one embodiment, the abundance of at least 20 genera of bacteria is determined.

The present disclosure also provides a method of determining a subtype of IBS in a subject, comprising determining an abundance of at least 5 species of bacteria in a sample from the subject or the subject's environment, wherein the at least 5 species of bacteria are selected from *Christensenella minuta, Papillibacter cinnamivorans, Bilophila wadsworthia, Ruminococcus bromii, Soleaferrea massiliensis, Akkermansia muciniphila, Oscillibacter valericigenes, Desulfitobacterium frappieri, Anaerofilum pentosovorans, Lactobacillus japonicas, Catabacter hongkongensis, Clostridium sporosphaeroides,* and *Faecalibacterium prausnitzii*.

In one embodiment, the at least 5 species of bacteria include at least 2 species selected from *Christensenella minuta, Papillibacter cinnamivorans, Bilophila wadsworthia, Ruminococcus bromii,* and *Soleaferrea massiliensis*.

In one embodiment, the at least 5 species of bacteria include *Christensenella minuta, Papillibacter cinnamivorans, Bilophila wadsworthia, Ruminococcus bromii,* and *Soleaferrea massiliensis*.

In one embodiment, the abundance of at least 10 species of bacteria is determined.

The present disclosure also provides a method of diagnosing autism, comprising determining an abundance of at least 10 genera of bacteria in a sample from a subject or the subject's environment, wherein the at least 10 genera are selected from *Ruminiclostridium, Sarcina, Lachnoclostridium, Asaccharospora, Lachnobacterium, Anaerostipes, Faecalibacterium, Bacteroides, Mogibacterium, Haemophilus, Intestinibacter, Mobiluncus, Lactobacillus, Alistipes, Dorea, Ferrimonas, Romboutsia, Actinobacillus, Anaerofilum, Erwinia, Phascolarctobacterium, Selenomonas, Microbacterium, Ureibacillus, Proteus, Megamonas, Christensenella, Butyricimonas, Arcobacter, Yersinia, Lachnoanaerobaculum, Variovorax, Citrobacter, Paenibacillus, Anaeroplasma, Fictibacillus, Eisenbergiella, Lautropia,* and *Howardella*.

In one embodiment, the at least 10 genera of bacteria include at least 5 genera selected from *Ruminiclostridium, Sarcina, Lachnoclostridium, Asaccharospora, Lachnobacterium, Anaerostipes, Faecalibacterium, Bacteroides, Mogibacterium,* and *Haemophilus*.

In one embodiment, the at least 10 genera of bacteria include *Ruminiclostridium, Sarcina, Lachnoclostridium, Asaccharospora, Lachnobacterium, Anaerostipes, Faecalibacterium, Bacteroides, Mogibacterium,* and *Haemophilus*.

In one embodiment, the abundance of at least 20 genera of bacteria is determined. In one embodiment, the abundance of at least 30 genera of bacteria is determined.

The present disclosure also provides a method of diagnosing a dysbiosis in a subject, comprising determining an abundance of at least 5 species of bacteria in a sample from the subject, wherein the at least 5 species of bacteria are selected from *Corynebacterium minutissimum, Prevotella oulora, Fusobacterium naviforme, Prevotella ruminicola, Bifidobacterium thermacidophilum, Dysgonomonas wimpennyi, Propionibacterium acnes, Corynebacterium tuberculostearicum, Brevibacterium casei, Lachnobacterium bovis, Prevotella dentasini, Prevotella albensis, Veillonella atypica, Kytococcus schroeteri, Prevotella copri, Bacteroides barnesiae, Prevotella conceptionensis, Anaerofustis stercorihominis, Bifidobacterium thermophilum, Prevotella brevis, Roseburia intestinalis, Clostridium symbiosum, Barnesiella intestinihominis, Bacteroides fragilis, Anaerostipes rhamnosus, Collinsella aerofaciens, Clostridium bolteae, Arthrobacter creatinolyticus, Atopobium fossor, Prevotella paludivivens,* and *Pelotomaculum isophthalicicum*.

In one embodiment, the at least 5 species include at least 2 species selected from *Corynebacterium minutissimum, Prevotella oulora, Fusobacterium naviforme, Prevotella ruminicola*, and *Bifidobacterium thermacidophilum*.

In one embodiment, the at least 5 species include *Corynebacterium minutissimum, Prevotella oulora, Fusobacterium naviforme, Prevotella ruminicola*, and *Bifidobacterium thermacidophilum*.

In one embodiment, the abundance of at least 10 species of bacteria is determined. In one embodiment, the abundance of at least 20 species of bacteria is determined.

The present disclosure also provides a method of diagnosing a dysbiosis in a subject, comprising determining an abundance of at least 5 genera of bacteria in a sample from the subject, wherein the at least 5 genera of bacteria are selected from *Corynebacterium, Lachnobacterium, Propionibacterium, Kytococcus, Fusobacterium, Veillonella, Prevotella, Anaerofustis, Arthrobacter, Dysgonomonas, Calothrix, Atopobium, Brevibacterium, Micrococcus, Burkholderia, Veillonella, Pelotomaculum, Acidaminococcus, Mitsuokella, Allisonella, Odoribacter, Bacteroides,* Coprobacter, *Alistipes, Ruminococcus, Ferrimonas, Alkaliphilus*, and *Lautropia*.

In one embodiment, the at least 5 genera include at least 2 genera selected from *Corynebacterium, Lachnobacterium, Propionibacterium, Kytococcus*, and *Fusobacterium*.

In one embodiment, the at least 5 genera include *Corynebacterium, Lachnobacterium, Propionibacterium, Kytococcus*, and *Fusobacterium*.

In one embodiment, the abundance of at least 10 genera of bacteria is determined. In one embodiment, the abundance of at least 20 genera of bacteria is determined.

In one embodiment, the dysbiosis is IBS.

The present disclosure also provides a method of determining a subtype of IBS in a subject with IBS, comprising determining an abundance of at least 5 species of bacteria in a sample from the subject, wherein the at least 5 species of bacteria are selected from *Christensenella minuta, Soleaferrea massiliensis, Papillibacter cinnamivorans, Oscillibacter valericigenes, Ruminococcus bromii, Gemmiger formicilis, Desulfitobacterium frappieri, Alistipes obesi, Anaerofilum pentosovorans, Akkermansia muciniphila, Alkaliphilus crotonatoxidans, Eubacterium sulci, Bdellovibrio exovorus, Curtobacterium pusillum, Flavonifractor plautii, Ruminococcus lactaris, Mogibacterium neglectum, Roseburia inulinivorans, Butyricimonas virosa, Intestinimonas butyriciproducens, Butyrivibrio crossotus, Barnesiella intestinihominis, Flavobacterium resistens, Flavobacterium cauense, Clostridium glycyrrhizinilyticum, Anaerostipes hadrus, Prevotella ruminicola, Blautia wexlerae*, and *Anaerostipes coli*.

In one embodiment, the at least 5 species of bacteria include at least 2 species selected from *Christensenella minuta, Soleaferrea massiliensis, Papillibacter cinnamivorans, Oscillibacter valericigenes*, and *Ruminococcus bromii*.

In one embodiment, the at least 5 species of bacteria include *Christensenella minuta, Soleaferrea massiliensis, Papillibacter cinnamivorans, Oscillibacter valericigenes*, and *Ruminococcus bromii*.

In one embodiment, the abundance of at least 10 species of bacteria is determined. In one embodiment, the abundance of at least 20 species of bacteria is determined.

The present disclosure also provides a method comprising diagnosing IBS in a subject according to the methods described herein and, if the subject is diagnosed with IBS, subsequently determining the subtype of IBS according to the methods described herein.

The present disclosure also provides a method of determining a subtype of IBS in a subject who has been diagnosed with IBS-M, comprising determining an abundance of at least 5 species of bacteria in a sample from the subject and assigning the subject as having constipation-dominant IBS-M (IBS-MC) or diarrhoea-dominant IBS-M (IBS-MD) based on the abundance of the at least 5 species of bacteria.

In one embodiment, the at least 5 species of bacteria are selected from *Peptoniphilus coxii, Clostridium clariflavum, Bacteroides thetaiotaomicron, Bacteroides coprocola, Oscillibacter valericigenes, Clostridium hveragerdense, Ruminiclostridium clariflavum, Bacteroides xylanisolvens, Clostridium chauvoei, Clostridium tepidiprofundi, Papillibacter cinnamivorans, Lactococcus fujiensis, Bacteroides uniformis, Bacillus thuringiensis, Johnsonella ignava, Pseudoflavonifractor capillosus, Christensenella minuta, Enterococcus azikeevi, Intestinimonas butyriciproducens, Eubacterium sulci, Flavobacterium resistens, Anaerotruncus colihominis, Pseudoflavonifractor capillosus, Bacteroides fluxus, Ruminococcus lactaris, Butyrivibrio crossotus, Eubacterium rectale, Prevotella ruminicola, Gemmiger formicilis, Ruminococcus flavefaciens*, and *Faecalibacterium prausnitzii*.

In one embodiment, the at least 5 species of bacteria include at least 2 species selected from *Peptoniphilus coxii, Clostridium clariflavum, Bacteroides thetaiotaomicron, Bacteroides coprocola*, and *Oscillibacter valericigenes*.

In one embodiment, the at least 5 species of bacteria include *Peptoniphilus coxii, Clostridium clariflavum, Bacteroides thetaiotaomicron, Bacteroides coprocola*, and *Oscillibacter valericigenes*.

In one embodiment, the abundance of at least 10 species of bacteria is determined. In one embodiment, the abundance of at least 20 species of bacteria is determined.

The present disclosure also provides a method of diagnosing autism in a subject with IBS, comprising determining an abundance of at least 5 species of bacteria in a sample from the subject, wherein the at least 5 species of bacteria are selected from *Eubacterium hallii, Eubacterium rectale, Lachnobacterium bovis, Lachnoclostridium glycyrrhizinilyticum, Blautia glucerasea, Eubacterium desmolans, Anoxystipes fissicatena, Blautia coccoides, Faecalibacterium prausnitzii, Clostridium symbiosum, Roseburia inulinivorans, Anaerostipes coli, Coprococcus comes, Lachnospira pectinoschiza, Arthrobacter creatinolyticus, Clostridium nexile, Bifidobacterium thermacidophilum, Anaerostipes rhamnosus, Clostridium clariflavum, Blautia wexlerae, Fusicatenibacter saccharivorans, Tolumonas auensis, Ruminococcus gnavus, Peptococcus niger, Dorea formicigenerans, Roseburia intestinalis, Blautia wexlerae, Clostridium populeti, Dorea massiliensis*, and *Eubacterium eligens*.

In one embodiment, the at least 5 species of bacteria include at least 2 species selected from *Eubacterium hallii, Eubacterium rectale, Lachnobacterium bovis, Lachnoclostridium glycyrrhizinilyticum*, and *Blautia glucerasea*.

In one embodiment, the at least 5 species of bacteria include *Eubacterium hallii, Eubacterium rectale, Lachnobacterium bovis, Lachnoclostridium glycyrrhizinilyticum*, and *Blautia glucerasea*.

In one embodiment, the abundance of at least 10 species of bacteria is determined. In one embodiment, the abundance of at least 20 species of bacteria is determined.

The present disclosure also provides a method of diagnosing a dysbiosis associated with intestinal senescence, the method comprising determining an abundance of at least 5 species of bacteria in a sample from the subject, wherein the at least 5 species of bacteria are selected from *Pseudobutyrivibrio xylanivorans, Dorea massiliensis, Blautia glucerasea, Lachnoclostridium herbivorans, Faecalibacterium prausnitzii, Romboutsia lituseburense, Peptoniphilus methioninivorax, Blautia coccoides, Megamonas funiformis, Eubacterium rectale, Clostridium bifermentans, Roseburia intestinalis, Clostridium populeti, Clostridium hiranonis, Peptoclostridium difficile, Lactonifactor longoviformis, Clostridium caliptrosporum, Asaccharospora irregulare, Clostridium malenominatum, Clostridium symbiosum, Clostridium thermoalcaliphilum, Lachnoclostridium glycyrrhizinilyticum, Ruminococcus faecis, Blautia schinkii, Pseudoflavonifractor capillosus, Clostridium chromoreductans, Clostridium ghonii, Clostridium innocuum, Christensenella minuta, Dorea formicigenerans*, and *Clostridium tertium*.

In one embodiment, the at least 5 species of bacteria include at least 2 species selected from *Pseudobutyrivibrio xylanivorans, Dorea massiliensis, Blautia glucerasea, Lachnoclostridium herbivorans*, and *Faecalibacterium prausnitzii*.

In one embodiment, the at least 5 species of bacteria include *Pseudobutyrivibrio xylanivorans, Dorea massiliensis, Blautia glucerasea, Lachnoclostridium herbivorans*, and *Faecalibacterium prausnitzii*.

In one embodiment, the abundance of at least 10 species of bacteria is determined. In one embodiment, the abundance of at least 20 species of bacteria is determined.

The present disclosure also provides a method of treating a subject with a dysbiosis, comprising determining the subtype of IBS according to the methods described herein, or diagnosing the subject according to the methods described herein, and administering a composition to the subject which increases and/or decreases the abundance of one or more species of bacteria in the subject, thereby treating the subject.

In one embodiment, the composition is a nutraceutical. In one embodiment, the composition is a probiotic. In one embodiment, the composition is a faecal microbiota transplant.

The present disclosure also provides a method of monitoring effectiveness of the treatments described herein, comprising measuring the abundance of one or more species of bacteria in a sample from the subject, wherein an increase and/or decrease in the abundance of one or more species of bacteria is indicative of the effectiveness of the treatment.

The present disclosure also provides a method of determining a suitable treatment for a subject with a dysbiosis, comprising determining the subtype of IBS according to the methods described herein, or diagnosing the subject according to the methods described herein, and determining a suitable treatment based on the results of the determination of subtype of IBS or diagnosis.

In one embodiment, the subject is a human.

In one embodiment, the subject has previously been administered a chemotherapy or an antibiotic.

In one embodiment, the sample is a faecal sample.

The present disclosure also provides a method of diagnosing a dysbiosis in
a subject, comprising
i) aligning sequences of nucleic acids in a sample from the subject to a database of bacterial 16S rRNA sequences;
ii) using the alignment in step i) to determine the identity and relative abundance of one or more species of bacteria present in the sample; and
iii) comparing the abundance of the one or more species of bacteria in the sample to the abundance of the one or more species of bacteria in a reference population of healthy individuals,
wherein an increase or decrease in abundance of a species of bacteria in the sample relative to the reference population is indicative of a dysbiosis.

In one embodiment, the database essentially consists of 16S rRNA sequences from human gastrointestinal microbiota.

In one embodiment, the database consists of DNA sequences. In one embodiment, the database consists of RNA sequences.

In one embodiment, the reference population is age-matched to the subject.

In one embodiment, the sequences of nucleic acids in the sample are obtained by high-throughput nucleic acid sequencing.

In one embodiment, the identity and relative abundance of at least 50 species of bacteria in the sample is determined. In one embodiment, the identity and relative abundance of at least 100 species of bacteria in the sample is determined. In one embodiment, the identity and relative abundance of at least 200 species of bacteria in the sample is determined.

In one embodiment, the subject is a human. In one embodiment, the subject is a horse.

In one embodiment, the sample is a faecal sample. In one embodiment, the sample is obtained from the subject's mouth. In one embodiment, the sample is obtained from the subject's vagina. In one embodiment, the sample is obtained from the subject's surrounding environment.

In one embodiment, the dysbiosis is a dysbiosis of the gastrointestinal tract.

In one embodiment, the dysbiosis is associated with irritable bowel syndrome (IBS). In one embodiment, the dysbiosis is associated with an inflammatory disease. In one embodiment, the dysbiosis is associated with an immune disease. In one embodiment, the dysbiosis is associated with a metabolic disorder. In one embodiment, the dysbiosis is associated with autism. In one embodiment, the dysbiosis is associated with intestinal senescence. In one embodiment, the dysbiosis is associated with chronic fatigue.

In one embodiment, the subject has previously been administered a chemotherapy.

The present disclosure also provides a method of diagnosing a dysbiosis in a subject, comprising
i) aligning sequences of nucleic acids in a sample from the subject to a database of bacterial 16S rRNA sequences;
ii) using the alignment in step i) to determine the identity and relative abundance of one or more species of bacteria present in the sample, thereby obtaining a sample dataset; and
iii) applying a machine learning algorithm to the sample dataset to diagnose the dysbiosis in the subject,
wherein the machine learning algorithm has been trained with a training dataset comprising identities and abundances of bacterial species from a reference population comprising individuals having the dysbiosis.

In one embodiment, the machine learning algorithm is a Bayesian algorithm. In one embodiment, the machine learning algorithm is a Random Forest algorithm.

In one embodiment, the reference population further comprises healthy individuals.

DESCRIPTION OF EMBODIMENTS

General Techniques and Definitions

Figure 1:
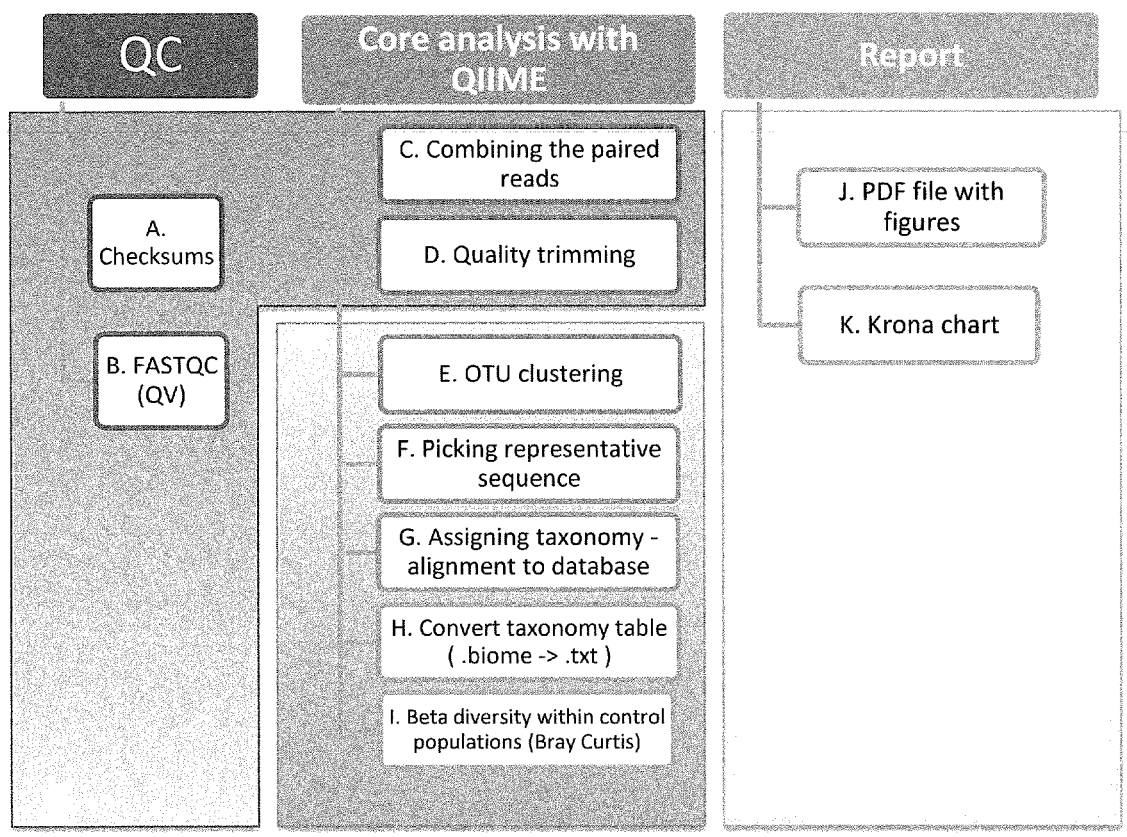
FIG. 1: Bioinformatics pipeline. Workflow for analysing nucleic acid sequencing data as described in Example 1.

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, group of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., molecular genetics, microbiology, nucleic acid sequencing, and biochemistry).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

As used herein, the phrase "nucleic acid sequence" refers to the linear sequence of nucleotides in a nucleic acid. The nucleic acid sequence can be either a DNA or RNA sequence.

As used herein, the term "sample" refers to a collection of biological material obtained from a subject or a subject's surrounding environment, such as soil or water in the area that the subject inhabits. In some embodiments, the sample is obtained from the subject. For example, the sample can be a faecal sample. In some embodiments the sample is obtained from the subjects' vagina, mouth or other orifice. The sample may be in a form taken directly from the subject or surrounding environment, or it may be at least partially purified to remove at least some non-nucleic acid material. The purification may be slight, for instance amounting to no more than the concentration of the solids, or cells, of the sample into a smaller volume or the separation of cells from some or all of the remainder of the sample. In some embodiments, nucleic acids are isolated from the sample. Such isolated preparations include reverse transcription products and/or PCR amplification products of the nucleic acids in the sample. In some embodiments, the predominant nucleic acid is DNA. The nucleic acid preparations can be pure or partially purified nucleic acid preparations. Techniques for the isolation of nucleic acid from samples, including complex samples, are numerous and well known in the art. Suitable techniques are described in WO98/51693 and WO01/53525.

As used herein, the term "subject" refers to any animal, including human and non-human animals. In some embodiments, the animal is a mammal. In some embodiments, the mammal is a human. In some embodiments, the mammal is a horse, cow, sheep, dog or cat. In some embodiments, the animal is a bird. In some embodiments, the bird is a chicken, duck, or turkey. Terms such as "subject", "patient" or "individual" are terms that can, in context, be used interchangeably in the present disclosure. In some embodiments, the subject is an adult or a child or a baby or a senior. The subject may have a disease or pathological condition. For example, in some embodiments, the subject has cancer.

As used herein, the term "reference population" refers to a collection of individuals to be compared to the subject. In some embodiments the reference population comprises healthy individuals. In some embodiments, the reference population comprises individuals having the dysbiosis to be diagnosed. In some embodiments the reference population comprises both healthy individuals and individuals having the dysbiosis to be diagnosed. In some embodiments the reference population is age-matched to subject. Therefore, in these embodiments, the subject is compared to a collection of individuals who are in a similar age category, e.g., baby, child, adult, or senior.

As used herein, the term "healthy individual" refers to an individual, human or non-human, who does not have any pathological condition, disease, or syndrome. Such individuals are useful for preparing a reference population for comparison to a subject.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present disclosure is performed without undue experimentation using, unless otherwise indicated, conventional techniques of molecular biology, recombinant DNA technology, and bioinformatics. Such procedures are described, for example, in (Sambrook & Green, 2012), (Glover, 1985), (Hames & Higgins, 1985), (Roig, 1985), (Perbal, 1984), and (Colowick & Kaplan, 1963).

Additional references that are useful for understanding bionformatic applications for nucleic acid sequence analysis, principle component analysis, machine learning and the like, include, (Hinchliffe, 1996), (Gibas & Jambeck, 2001), (Pevzner, 2000), (Durbin et al., 1998), and (Rashidi & Buehler, 2000).

Dysbiosis

As used herein, the term "dysbiosis" refers to a state of imbalance in the microbiome of a subject. In such cases, the microbiome of the subject differs or deviates from the microbiome that is typical of a normal, healthy individual. The extent of dysbiosis is a measure of how different a microbiome is from a normal microbiome. A dysbiosis therefore includes both an increase and/or decrease in abundance of one or more bacterial species relative to a microbiome of a healthy individual. In the context of diagnosis of diseases and conditions associated with perturbations in the microbiome, dysbiosis can be more specifically defined as a microbiome that differs from the microbiome of a subject who does not have the disease or condition or is not at risk of developing the disease or condition.

A "microbiome profile" is a profile of the relative abundances of a plurality of bacterial species in a sample. In accordance with the methods of the invention, a microbiome profile is a numerical representation of such abundances that has been obtained from an analysis of nucleic acids in a sample from a subject. The individual values for such abundances can be qualitative, quantitative or semi-quantitative. Terms such as "abundance", "level" or "amount" are terms that can, in context, be used interchangeably in the present disclosure.

A microbiome profile can comprise the abundance of each bacterial species identified in a sample, or it can comprise the total abundance of each bacterial genus identified in the sample, i.e., the sum of all species abundances for each genus.

In some embodiments, the dysbiosis is a gastrointestinal tract dysbiosis. As used herein, the term "gastrointestinal tract" refers to the digestive tract or alimentary canal, which is the continuous series of organs beginning at the mouth and ending at the anus. The gastrointestinal tract is colonised by a variety of different species of bacteria and other microorganisms. The total microorganism content of the gastrointestinal tract is referred to as gastrointestinal microbiota.

In some embodiments, the dysbiosis is associated with a particular condition or disease. It is known in the art that a dysbiosis can be associated with a number of varying diseases and conditions. Such diseases and conditions include both intestinal and extra-intestinal disorders, such as irritable bowel syndrome (IBS), inflammatory bowel disease (IBD), autism, immune disorders including coeliac disease, allergy, asthma, metabolic disorders, inflammatory diseases, cardiovascular disease, and obesity. In some embodiments, the dysbiosis is associated with IBS or a particular subtype of IBS. In some embodiments, the dysbiosis is associated with an inflammatory disease. In some embodiments, the dysbiosis is associated with an immune disease. In some embodiments, the dysbiosis is associated with a metabolic disorder. In some embodiments, the dysbiosis is associated with autism. In some embodiments, the subject has cancer. In some embodiments, the dysbiosis is associated with intestinal senescence.

The methods described herein are able to provide diagnosis of a subject in a fast, objective, and/or accurate manner and thus offer the opportunity to continually monitor the degree of dysbiosis in a subject and develop personalised medical treatments for subjects diagnosed with the dysbiosis. The methods of the present invention can therefore be incorporated as part of a patient management scheme, which encompasses diagnosis, disease monitoring, determining suitable treatment regimes, treating a subject, and measuring a subject's response to therapy. Accordingly, in some embodiments, the methods of the present invention comprise treating the subject by administering a composition which increases and/or decreases the relative abundance of one or more species of bacteria in the subject's microbiome. Suitable compositions include, but are not limited to nutraceuticals, pharmaceuticals, faecal microbiota transplants, phytochemicals, fermented foods or beverages, plants or plant extracts, invertebrate organisms, prebiotics, and probiotics. The composition to be administered can be selected based on the species of bacteria whose abundance is causing the dysbiosis, which is identified by utilising the methods of the present invention.

In some embodiments, the subject has previously been administered a treatment for a disease. For example, the treatment can be a chemotherapy. Thus, in some embodiments, the methods of the present invention are useful in monitoring changes in a subject's microbiome that may occur as a result of a treatment.

In some embodiments, the methods described herein comprise administering a nutraceutical, in order to treat the dysbiosis or associated condition. As used herein, the term "nutraceutical" refers a pharmaceutical grade dietary supplement or food additive that can be administered in a purified form, i.e., in a liquid or capsule, or incorporated into food. In some embodiments, the nutraceutical comprises a phytochemical.

In some embodiments, the methods described herein comprise administering a faecal microbiota transplant. As is known in the art, a faecal microbiota transplant is the process of transplantation of faecal bacteria from a healthy individual into a subject. Faecal bacteria, obtained from a healthy individual can be introduced to the subject through infusion of stool, e.g. by enema, orogastric tube or by mouth in the form of a capsule containing freeze-dried material.

Irritable Bowel Syndrome (IBS)

In some embodiments, the dysbiosis is irritable bowel syndrome (B S). IBS is a condition that affects the functioning of a subject's bowel. IBS is manifested by a group of symptoms, including abdominal pain and changes in the pattern of bowel movements, often without any evidence of underlying damage to the bowel. Traditionally, IBS has been classified into four main subtypes according to "Rome IV" criteria depending on whether diarrhoea is common, constipation is common, both are common, or neither occurs very often; these subtypes are IBS-D, IBS-C, IBS-M, or IBS-U respectively. In this regard, the Rome IV IBS subtypes are based on how frequently a subject experiences very loose or very hard stools. Conventionally, a subject is assigned to one of these subtypes based on the appearance of their stool samples and/or by filling out a questionnaire.

The type, quantity, intensity, and severity of symptoms vary from subject to subject. Furthermore, IBS subtype can be re-classified as a subject's bowel habits change over time. It is therefore difficult to accurately determine the subtype of IBS in a subject using conventional methods. The present disclosure relates to, in part, methods for diagnosing and/or determining the subtype of IBS in a subject which are based on an assessment of the abundance of particular bacteria in the subject's microbiome. Furthermore, the present inventors have surprisingly found that subjects who have been diagnosed with IBS-M can be further assigned into constipation-dominant IBS-M, referred to herein as "IBS-MC", or diarrhoea-dominant IBS-M, referred to herein as "IBS-MD", by measuring the abundance of at least five species of bacteria in the subject's microbiome. Such methods enable the establishment of more targeted and/or personalised medical treatment protocols, for example identification of suitable probiotics, for subjects with IBS.

Methods of Determining the Identity and Abundance of Bacteria in a Sample

A microbiome profile can be obtained by any convenient means through which the identity and abundance of bacterial species in a sample may be measured and/or quantified. The abundance of a bacterial species can be measured by any suitable method. Suitable methods include but are not limited to nucleic acid analysis (including nucleic acid sequencing, oligonucleotide probe hybridisation, and primer based nucleic acid amplification approaches), antibody binding or other specific affinity ligand based approaches, proteomic and metabolomic approaches. In some embodiments the abundance of bacterial species is measured by analysing nucleic acid sequencing data.

The Sanger dideoxynucleotide sequencing method is a technique for sequencing nucleic acids, which is well known in the art. More recently "high-throughput sequencing" approaches, also known as "next generation" or "second generation" sequencing have been developed. These more recent techniques are characterised by having a high throughput, in that they utilise parallel (e.g. "massively parallel") sequencing reactions, or less time-consuming steps to obtain the sequences of multiple nucleic acids in a sample. Various high-throughput sequencing methods provide single molecule sequencing and employ techniques such as pyrosequencing, reversible dye terminator sequencing, cleavable probe sequencing by ligation, non-cleavable probe sequencing by ligation, DNA nanoballs, and real-time single molecule sequencing.

In some embodiments, the sequences of nucleic acids in the sample are obtained by high-throughput sequencing. For example, the sequences of nucleic acids can be obtained by Illumina™ sequencing, which utilises reversible dye terminators. Suitable instruments for conducting high-throughput sequencing are known in the art, these include, but are not limited to, the MiSeq™ instrument (Illumina™).

In order to determine the identity and abundance of species of bacteria in a sample, a sequence alignment between the nucleic acid sequencing reads and known bacterial sequences can be performed. The alignment can be performed between RNA or DNA sequences. Methods for aligning nucleic acid sequences will be well known to those skilled in the art. A variety of programs which implement sequence alignment algorithms for such comparisons are known in the art and are freely available. Some of these programs utilise Needleman and Wunsch or Smith and Waterman algorithms. These algorithms are implemented by the following programs: PileUp (Feng & Doolittle, 1987; Higgins & Sharp, 1989), Gap and BestFit (Needleman & Wunsch, 1970), as part of the GCG software suite (Genetics Computer Group, 575 Science Drive, Madison, Wis., USA 53711, 1991), and "water" of Emboss WIN (version 2.10.0). Other suitable software for entering and aligning or otherwise manipulating nucleic acid sequences is freely available, e.g., BLASTN (NCIMB, https://blast.ncbi.nlm.nih.gov), or can easily be constructed from open source code by one of skill using a standard programming language such as Visualbasic, Fortran, Basic, Java, R, Python, C++ or the like.

The successful alignment between a query sequence from the sample, and a known bacterial sequence (an alignment resulting in a sequence identity over a given threshold) is indicative of the presence of that bacterium in the sample. Therefore, the sequence alignment can be used to determine the identity of the species of bacteria in the sample. In some embodiments, the sequences of nucleic acids in the sample are aligned to known bacterial 16S rRNA sequences. The sequences of the nucleic acids from the sample can be aligned directly to the 16S rRNA sequences or to DNA sequences encoding 16S rRNA. 16S rRNA is the RNA component of the prokaryotic ribosome small subunit which binds to the Shine-Dalgarno sequence in a mRNA target during ribosome recruitment. The genes encoding 16S rRNA are used in reconstructing phylogenies, due to the slow rates of evolution of this region of the gene. 16S rRNA sequences are therefore useful for identifying which species of bacteria are present in a sample. Over several thousands of microbial genomes have been sequenced and sequences of 16S rRNA are publicly available (see http://genomesonline.org or http://www.ncbi.nlm.nih.gov). Several public ongoing projects have aimed to sequence the entire microbial DNA present in an ecosystem, such as the Human Microbiome Project (see http://nihroadmap.nih.gov/hmp/).

In some embodiments, the abundance of each of the bacterial species identified in the sample is calculated from the number of sequencing reads of a particular sequence that were observed during nucleic acid sequencing. For a given nucleic acid sequence, the number of sequencing reads observed corresponds to the number of times the sequencing instrument detected that sequence. Therefore, the number of sequencing reads is correlated with the number of times that nucleic acid sequence appears in the sample, which is in turn correlated with the abundance of the species of bacteria that the nucleic acid originated from.

In some embodiments, the abundance of bacterial species in a sample can be obtained using a oligonucleotide hybridisation probe based approach, such as a microarray. In such approaches, the presence and amount of a target nucleotide sequence is measured by detecting a specific hybridisation event between a nucleic acid probe and its target sequence. Suitable hybridisation conditions are described in (Sambrook & Green, 2012), (Berger & Kimmel, 1987), (Young & Davis, 1983), and (Thijssen, 1993). The nucleic acid probes can be provided as part of a wider array, e.g. an immobilised nucleic acid microarray. Suitable methods are described in WO2012080754 and WO201 1043654.

In some embodiments the bacterial species for which the relative abundance thereof are to be determined are preselected. For instance, the relative abundance of certain bacteria can be indicative and/or causative of a disease which is associated with a dysbiosis. Thus, in some embodiments, the abundance of each of the bacterial species identified in the sample can be calculated using quantitative nucleic acid-based amplification reactions. These include the Polymerase Chain Reaction (PCR) and Ligase Chain Reaction (LCR) and modifications thereof, such as Reverse Transcription PCR see (McPherson & Moller, 2006), and (Wiedman et al., 1994).

Database of Bacterial 16S rRNA Sequences

In some embodiments, the nucleic acid sequences in the sample are aligned to a database of bacterial 16S rRNA sequences. The database can comprise RNA sequences or DNA sequences encoding the RNA. Furthermore, the database can comprise known 16rRNA sequences from a plurality of different bacterial species. In such embodiments, each unique nucleic acid sequence in the sample is aligned to the nucleic acid sequences in the database, in order to determine the best matching sequence, thereby determining the identity of the bacterial species that the nucleic acid in the sample originated from.

Suitable publicly available databases comprising over a million known bacterial 16S rRNA sequences include, but are not limited to, SILVA (http://www.arb-silva.de; Pruesse et al., 2007), RDP (http://rdp.cmu.mse.edu, Cole et al., 2008), and GreenGene (http://greengenes.lbl.gov).

The collection of reference sequences in the database is important for the reliable identification of the bacterial nucleic acid sequences in the sample. The databases described above are oriented towards comprehensive taxonomic profiling of microbial ecosystems from wide range of ecological sources. Such a wide range of bacterial sequences may not be adequate in embodiments for which identification of bacterial species in the human gastrointestinal microbiota is required. This is because the over representation of similar sequences from species which do not inhabit the human gastrointestinal tract may challenge the computational algorithms for the selection of the closest sequence match. One of the solutions to address this misclassification problem is to use a dedicated database which contains only nucleic acid sequences from bacterial species that are found in the human gastrointestinal tract. Therefore, in some embodiments, the database of bacterial 16S rRNA sequences essentially consists of nucleic acid sequences from human gastrointestinal microbiota. Suitable databases include, but are not limited to the publically available HITdb database (https://www.ncbi.nlm.nih.gov/pmc/articles/PMC4676846). This database is a dedicated collection of ~2,473 unique prokaryotic species-like groups and their taxonomic lineages from human intestinal microbiota.

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Sequel™, Oracle™, Paradox™) can be adapted to the present disclosure in order to edit, curate, or construct suitable databases. For example, the systems can include software having the appropriate character string information, e.g., used in conjunction with a user interface (e.g., a GUI in a standard operating system such as a Windows, Macintosh or LINUX system) to manipulate strings of characters.

As noted, systems can include a computer with an appropriate database, as described above. Software for manipulating and aligning nucleic acid sequences, as well as data sets entered into the software system comprising any of the nucleic acid sequences described herein can be a feature of the disclosure. The computer can be, e.g., a PC (Intel x86 or Pentium chip-compatible DOS™, OS2™ WINDOWS™ WINDOWS NT™, WINDOWS95™, WINDOWS98™, WINDOWS2000, WINDOWSME, or LINUX based machine, a MACINTOSH™, Power PC, or a UNIX based (e.g., SUN™ work station or LINUX based machine) or other commercially available computer which is known to one of skill.

Machine Learning Algorithms

In some embodiments, a computer-implemented machine learning algorithm is utilised in order to diagnose the dysbiosis. Such algorithms use relationships between a microbiome and a dysbiosis (or associated disease) which are observed in a training dataset from a reference population (with known disease status) in order to determine the overall likelihood of a subject (with unknown disease status) having a dysbiosis or associated disease. Machine learning algorithms are well known in the art and are described in detail in (Rasmussen and & Williams, 2005) and (Barber, 2012). Machine learning algorithms, include supervised machine learning (e.g. naïve Bayes classifiers, decision trees such as Random Forest, nearest neighbour, support vector machines, neural networks, etc.) and unsupervised machine learning (e.g., clustering, principal component analysis, etc.).

In some embodiments, the machine learning algorithm is a Bayesian algorithm, such as a naïve Bayes classifier, which are described in (Barber, 2012). Suitable freely available Bayesian algorithms will be known to those skilled in art and include R package 'e1071' version 1.6-7 "Misc Functions of the Department of Statistics, Probability Theory Group (Formerly: E1071) TU Wien, python package "NaiveBayes" (https://pypi.python.org/pypi/NaiveBayes), or the C++ program "Naive Bayes Classifier" (http://www.openpr.org.cn/index.php/NLP-Toolkit-for-Natural-Language-Processing/43-Naive-Bayes-Classfier/View-details.html).

In some embodiments, the machine learning algorithm is a Random Forest algorithm, which are described in (Ho, 1995) and (Caruana & Niculescu-Mizil, 2006). Suitable freely available Random Forest algorithms will be known to those skilled in art and include "The Original RF" (http://www.stat.berkeley.edu/~breiman/RandomForests/cc_software.htm), ALGLIB (http://www.alglib.net/dataanalysis/decisionforest.php), and R package "randomForest" (https://cran.r-project.org/web/packages/randomForest/index.html).

In some embodiments, limma is used to analyse nucleic acid sequencing data in order to determine the likelihood of a subject having a dysbiosis. Also, limma can be used to determine the species of bacteria whose abundance is most indicative of whether or not a subject has a dysbiosis. limma is a R/Bioconductor software package comprising multiple statistical algorithms for analysing nucleic acid sequencing data. The limma software is described in (Rithie et al., 2015) and is freely available as part of the Bioconductor project (http://www.bioconductor.org).

Example 1 Bioinformatics Pipeline

The "Bioinformatics pipeline" is a set of computational tasks that were sequentially applied to raw nucleic acid sequencing data in the form of FASTQ files, which were produced by the MiSeq (Illumina) high-throughput sequencing instrument. A set of informatics procedures were implemented into the pipeline for consistency, which improved the reproducibility and validity of the results. Open source programs and databases were used in the pipeline. An overview of the bioinformatics pipeline is presented in FIG. 1.

Primary Quality Control Analysis of Raw FASTQ Files

The raw sequences from individual samples analysed in the MiSeq instrument were in FASTQ format (fastq.gz). The sequences for each sample were supplied in two compressed FASTQ files; one for forward strand reads and the other for the reverse stand reads.

The downloaded FASTQ files were checked for integrity using the ExactFile program based on an MD5 sums algorithm (FIG. 1, Box A). Each of two FASTQ files for each individual sample were processed with the FASTQC program. A Perl script was used to run this program in a processing bulk mode which generated a brief report for each file (FIG. 1, Box B). The following key checkpoints were reported:

The number of raw reads. This number was expected to be over 30,000 for each sample.
 The quality of the first read. This must pass or have a Quality Value (QV) bin flag which begins no earlier than 280 bases in the analysed sequence. This means that the phred quality median or sequencing quality did not drop below 20 before the first 280 bases.

The Quality of the first read. This must pass or have a QV bin flag which begins no earlier than 250 bases in the analysed sequence. This means that the phred quality median or sequencing quality has not dropped below 20 before the first 250 bases.

The Library GC content should be in range 50-60%.

Any deviation from the stated quality control metrics above had a negative effect on the performance of the pipeline. Samples that did not meet the above criteria were identified as outliers relative to the bacterial classification profile.

The Core 16S Analysis with QIIME Workflow

QIIME™ stands for Quantitative Insights Into Microbial Ecology. QIIME is an open-source bioinformatics suite which was used for the microbiome analysis of the raw DNA sequencing data (http://qiime.org/). To accommodate the automatic processing of multiple samples through various QIIME steps a Perl script was developed with the following major steps:

Combining Paired Reads

Stitching of the paired reads was performed using the FLASH program (Fast Length Adjustment of SHort reads). This step is shown in FIG. 1, Box C. FLASH is a dedicated software tool for merging the paired-end reads from next-generation sequencing experiments (https://ccb.jhu.edu/software/FLASH/). The FLASH Program analysed the two FASTQ files and generated a single merged FASTQ file where the quality of the merged bases in the overlapping part of the sequence was assigned. Reads that were not merged were saved to separate files. The stitched reads and the forward reads from the non-combined sequences were pooled together into a new single FASTQ file. The second reads of non-combined sequences were discarded at this point in the pipeline. The following FLASH settings were altered from the default settings:

max-overlap: 150 max-mismatch-density: 0.33

The efficiency of the selected settings was established empirically and was shown to have the closest match to the commercial bioinformatics analysis software BaseSpace (Illumina).

Quality Trimming

Additional quality control filter was applied using the split_libraries.py command. This step is shown in FIG. 1, Box D. The following quality control parameters were used:

reads were removed if they were less than 150 bp in length, and the rest of the settings left to default thresholds.

This program converted FASTQ files to plain quality trimmed fasta files with .fna extensions.

Open Taxonomic Unit (OTU) Clustering

The quality trimmed and concatenated sequences were then run through a pairwise alignment and clustering. This is a process which queries a particular sequence against a target set of sequences recording the k-mers in common between the two sequences. Rather than inferring sequence similarity as the number of matching k-mers between a query and target sequence that determines the sequence similarity. USEARCH arranges the target sequences in decreasing order relative to the number of unique k-mers shared between the two sequences. The queried sequences were arranged into clusters. Each cluster or centroid shared a level of similarity below a set identity threshold level with each other centroid. The remaining query sequences were then assigned to a centroid (target sequence) based on an identity threshold using the USEARCH algorithm described above. If the query sequence did not share similarity with a centroid above the threshold, a new cluster was created. Picking was performed by using the pick_otus.py command with the default UCLUST algorithm (FIG. 1; Box E). The threshold for sequence similarity was 85%.

Picking Representative Sequence

The best sequence representing each cluster was selected for further taxonomy matching (FIG. 1, Box F). The best sequence in the cluster was the representative sequence or the seed sequence. This is a non-redundant sequence that has similarity to the rest of the sequence in the cluster with a defined threshold of 85%. This was representative of the longest sequences.

Assigning Taxonomy to a Database of 16S rRNA Sequences

Each representative sequence was searched and aligned against a database of bacterial 16S rRNA sequences, and the taxonomy of the best match was assigned to the cluster (FIG. 1, Box G). Typically, about 500 species were identified in each sample. The UCLUST algorithm described above used the USEARCH methodology. This process in QIIME received fasta sequence files as the input and produced a microbiome profile for each sample. The microbiome profile comprises the identities and abundances of bacteria present in the sample and is in the form of a biome format file (http://biom-format.org/). The relative abundance of each species of bacteria is estimated based on the number of sequencing reads. The Biome file was designed to be a general-use format for representing a biological sample by observation contingency tables. BIOM is a recognized standard for the Earth Microbiome Project and is a Genomics Standards Consortium supported project.

Converting the Taxonomy Table

The Biome file was then converted into a plain text file with QIIME command "biom convert". This text file was used for preparing a graphical summary and reports for the end user. To run the automated reports a Perl script was developed based on open source PDF libraries and CRAN R project programs. At the biom conversion step an additional denoising step could be added to the text file. This was an optional step. As a default setting, all the low abundant OTUs with the number of assigned reads below 10 were moved to an unclassified phylum bin. This step is shown in FIG. 1, Box H.

Beta Diversity in Relation to a Control Population

The Bacterial composition in two samples was compared with beta diversity statistics (index). One of the most popular indexes is Bray Curtis dissimilarity. This statistic was used to quantify the compositional dissimilarity between two different sites, based on counts at each site. It was a convenient measure of microbiome dissimilarity between two individuals as it is bound between 0 and 1. Where 0 means that the two individuals had the same composition (that is they shared all the species), and 1 means the two individuals did not share any species. At sites where the Bray Curtis index is intermediate (e.g. BC=0.5) this index differed from other commonly used indices because it also took in to account the relative species abundance. To compare a sample to the reference population pairwise, the Bray Curtis index was transformed to distance in R and plotted with "wcmdscale", Weighted Classical (Metric) Multidimensional Scaling method, implemented in the Vegan library. The idea is of this plot was to monitor how close one particular sample was in relation to the reference population (FIG. 1, Box I).

PDF Report with Figures

The abundance of the various important species and genera of bacteria was summarised by a Perl script. The output text files with species profile was the source for the Perl reporter script. Proportions of selected taxa were analysed in relation to a reference population. A bar chart and other graphics were generated in R with the automatics script. The produced figures and tables were then converted to a PDF report with a Perl script based on PDF::API2 library (FIG. 1, Box J).

Krona Chart

A Krona chart was generated using open source Krona tools (Ondov et al., 2011). The Krona visualization tool allowed the intuitive exploration of relative abundances and confidences within the complex hierarchies of metagenomic classifications. The Krona chart combined a variant of radial, space-filling displays with parametric colouring and interactive polar-coordinate zooming to visualise a dysbiosis in a subject's microbiome (FIG. 1, Box K).

Population Stratification by Age

Significant differences in the gut microbiome profiles were identified between individuals within some population sub-groups. A number of statistics were tested for correlation between microbiome profile and the sample meta data, including age, gender, time between collection and DNA extraction, and the batch number of generated sequences. The most significant differences in profiles were attributed to the age strata.

To produce an adequate profile comparison for the tested population the reference population was split into the following subgroups:

Newborn; aged up to 3 years;
Children; from 3 to 12 years,
Adults; from 12 to 60 years,
Seniors; over 60 years old.

Bacterial profiles for these groups were assessed separately for taxon distribution. New samples were tested according to population ranges from the appropriate age group.

Example 2 Diagnosis of a Dysbiosis in a Subject, Relative to Healthy Individuals Samples Faecal samples were collected using the DNA genotek OMNIgene•GUT (OMR-200) collection device which was used to stabilise the DNA for quantitative gut microbiome profile analysis. Upon receipt in the laboratory each faecal sample was frozen at −20° C. for no longer than 3 months. Each sample was prepared for the extraction process by taking a pea size sample and aliquoting the faecal material into a Pathogen Lysis tube (Cat No. ID: 19091 Qiagen). Each sample was centrifuged at 13,000 rpm for 5 minutes and the supernatant was discarded. For consistency, if required more solid faecal material was used to fill approximately half of the pathogen lysis tube. The Pathogen lysis tubes containing the faecal sample were then stored in the −20° C. freezer until further processing. The samples were processed in batch lots of forty-eight samples. The QIAamp PowerFecal DNA Kit (Cat No. ID: 12830-50 Qiagen) was used to extract DNA from the faecal samples. To ensure that each sample's biodiversity was analysed, the method utilised three steps to ensure that gram positive bacterial cell walls were lysed, bead beating (Tissue Lyser Qiagen), heating at 95° C. and Proteinase K (Cat. No 19133 Qiagen). The lysate material obtained was then processed on the QIAcube (Qiagen) using standard procedures. The extracted DNA was then frozen at −20° C. prior to high-throughput sequencing using the MiSeq system (Illumina) and analysis by the pipeline described in Example 1.

Reference Population of Healthy Individuals

To obtain a measure of dysbiosis, a reference population was required. Therefore, samples from a control group of healthy individuals were profiled using the pipeline described in Example 1. The abundances of each bacterium were summarized across the tested controls. This generated an abundance summary as shown in Table 1.

TABLE 1

Summary of vial output and visual inspection results

| | Min | Q1 | Q3 | Max |
|---|---|---|---|---|
| Eubacterium__ventriosum | 0.000156 | 0.000188 | 0.001688 | 0.003625 |
| Eubacterium__rectale__AY804151\|D = 90 | 9.38E-05 | 0.000211 | 0.00175 | 0.008938 |
| ... | | | | |
| OTU1210\|Bacteria X | 3.13E-05 | 0.000125 | 0.000531 | 0.001906 |
| OTU1315\|Bacteria Y | 3.13E-05 | 5.00E-04 | 0.001391 | 0.009188 |
| OTU1316\|Bacteria Z | 0 | 0.00025 | 0.001266 | 0.001906 |

Units are fraction of total bacterial abundance.

Comparison to a Sample from a Subject

The sample from a subject was then compared to the reference population profile. If the sample was interquartile i.e., between the Q3 and Q1 quantities it was labelled as "N" (normal) as it was amongst the majority (50%) of the reference population data. In the instance that a specimen was in the range between "Q3" and "Max" it was labelled as "Y", abundant yield. Samples having species with an abundance between "Min" and "Q1" were labelled "B" as basic depletion. Species having an abundance outside of control ranges were labelled as "S", specials. This produced a sample profile table (Table 2).

TABLE 2

Summary of the subject profile relative to reference population

| | profile |
|---|---|
| Eubacterium__ventriosum | B |
| Eubacterium__rectale__AY804151\|D = 90 | N |
| ... | |
| OTU1210\|Bacteria X | N |
| OTU1315\|Bacteria Y | P |
| OTU1316\|Bacteria Z | S |

Figure 2:
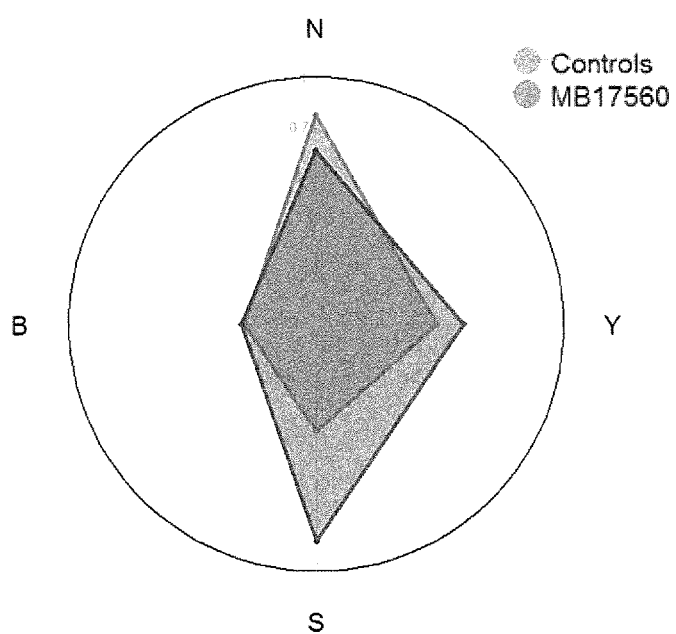
FIG. 2: Dysbiosis compass for a subject. Proportions of all types of matches: N, S, B, Y were summarized on the four axes (see Example 2). The plot illustrates that the microbiome of the subject was shifted away from the healthy zone which was assigned to the averaged control. The scales on chart are not required to be equal as the "N" scale is expected to be largest since the majority of the data should fall to "N" classification. Accordingly, the N scale can be between 0 and 1 and other scales can be 0 to 0.3.

This profile was also plotted as a "Dysbiosis compass" on a radar chart where proportions of all types of matches: N, S, B, Y were summarized on the four axes (FIG. 2). The plot in FIG. 2 illustrates that the bacterial balance of the subject sample is shifted away from the healthy green zone which was assigned to the averaged Control, which is therefore indicative of a dysbiosis. The control was derived from the reference population of healthy individuals described above. This shift towards "S" indicated a 3 fold increase in the amount bacteria with an abundance outside of the normal ranges (outside Min and Max). There was also a noticeable increase in "Y" direction which relates to those species that fell between Max and Q3. There was no change in low abundance species in the "B" direction numbers, which relate to bacteria in blue zone: between "Min" and "Q1".

Gut Microbiota Association

A number of pathological conditions were identified as having an association with depletion or increased relative abundance of particular bacteria in a subject's microbiome. These associations are summarised in Table 3 below.

groups of individuals with known IBS subtypes, which could be used to predict the subtypes in individuals whose subtype of IBS was not known. In this case, a naïve Bayes classifier was used as it demonstrated an improved performance when compared with other algorithms. Bayes classifiers are known to be used in diverse areas such as spam filtering procedures, automated medical diagnosis, and text categorization problems. The program implemented in R package 'e1071' version 1.6-7 "Misc Functions of the Department of Statistics, Probability Theory Group (Formerly: E1071), TU Wien was used.

TABLE 3

Gut microbiota association table

|  | IBS-D | IBS-M | IBS-C | IBS | Inflammation | Immune modulation | Metabolic disorders | Autism |
|---|---|---|---|---|---|---|---|---|
| Bacteroidetes Phylum | H | H | H |  |  |  |  |  |
| *Bacteroides* spp | H | H | H | L | LH | L | LH |  |
| *Bacteroides vulgatus* | H | H | H |  |  | LH |  | H |
| *Barnesiella* spp | L | H | L |  |  | L |  |  |
| *Odoribacter* spp | H | H | H |  | L |  |  |  |
| *Prevotella* spp | H | H | H |  | H | H | H | L |
| Firmicutes Phylum | L | L | L |  |  |  |  |  |
| *Anaerotruncus colihominis* | L |  |  |  |  |  | L |  |
| *Butyrivibrio crossotus* | H | H | H |  |  |  | L |  |
| *Clostridium* spp | L | L | L |  | LH |  |  | H |
| *Coprococcus eutactus* |  |  |  | L |  |  |  |  |
| *Faecalibacterium_prausnitzii* |  | L |  |  | LH |  |  | L |
| *Lactobacillus* spp | L | L | L | LH |  |  | H |  |
| *Roseburia* spp | H |  | L | L | L | L | L | L |
| *Ruminococcus* spp | L | L | L | LH | H |  |  |  |
| *Veillonella* spp | L |  | L | LH |  |  |  |  |
| Actinobateria Phylum | L |  | L |  |  |  |  |  |
| *Bifidobacterium* spp | H | H | L | L | L | L | LH | L |
| *Bifidobacterium longum* | L |  | L |  |  |  | H |  |
| *Collinsella aerofaciens* | L | L | L | L | H |  | H |  |
| Proteobacteria Phylum | H |  | H |  |  |  |  |  |
| *Desulfovibrio piger* | L |  | L | H | H |  |  | H |
| *Escherichia coli* "SmartDNA0001|ShigellaOrEColiLike" |  | H | H | H |  |  | H |  |
| *Escherichia coli + Shigella* |  |  | H |  |  |  |  |  |
| *Bilophila wadsworthia* | L | L | L |  |  |  |  |  |
| *Oxalobacter formigenes* | L | H |  |  |  |  | L |  |
| Fusobacteria Phylum | L |  |  |  |  |  |  |  |
| *Fusobacterium* spp |  |  |  |  | H | H | H |  |
| Verrucomicrobia Phylum | L | H |  |  |  |  |  |  |
| *Akkermansia muciniphila* | L | H |  | L |  |  | L | L |

L = Low: This indicates that patients with the condition had an abundance of that bacteria which was lower than 50% of the reference population.
H = High: This indicates that patients with the condition had an abundance of that bacteria which was higher than 50% of the reference population.

The gut microbiota association table enabled the diagnosis of particular pathological conditions, based on the dysbiosis of bacteria known to be associated with that condition.

Example 3 IBS Subtype Prediction

Prediction modelling using machine learning algorithms and supervised classification, such as Random Forest and Naïve Bayes algorithms, were used to predict IBS subtypes: IBS-D (diarrhoea), IBS-C (constipation), and IBS-M (mixed). A training data set was produced using microbiome profiles from individuals classified by clinicians into the three subtypes using Rome IV criteria:

IBS-D (diarrhoea), n=78
IBS-M (mixed), n=22
IBS-C (constipation), n=78

The purpose of the prediction algorithm was to detect reproducible differences in microbiome profiles across the The training dataset was produced using the microbiome profiles obtained from faecal samples of individuals with known IBS subtypes, using the methods described in Example 1. The training data contained a complete set of the DNA sequences which passed the sequencing quality control for each individual (unfiltered set). Microbiome profiles for each individual were combined at the species level of taxonomy classification. This generated a matrix of 1,756 identified species in the 178 faecal samples obtained from the individuals with known IBS subtypes (IBS-D n=78; IBS-M n=22; IBS-D n=78). This matrix was used to train a naïve Bayes model by function. The trained model was then applied back to the training data itself, which resulted in 89% (158/178) of samples being assigned to the correct subtype:

```
          C     D     M    |
    C    75    10     7    |  78
    D     3    68     3    |  68
    M     0     0    12    |  12
    _____    +  ___
    Correctly  predicted   | 158
```

The vertical columns in the plot above are the original groups. The horizontal rows are the predicted subtypes. The yellow highlighted samples are those which were assigned to the correct subtype.

Rarefied data was used to test the model performance on a mock sample set. For this purpose the original nonfiltered sequence dataset was reduced to 32,000 of random reads. The number of reads was taken regardless of the original amount of sequences produced for each particular sample. For some samples that was approximately less than 15% of the sequencing data. The rarefied dataset had a smaller number of identified species (1,649) when compared to the full data set (1,756). This was expected as some rare species may not be picked since they may be represented by very small number of sequence reads. Applying this new rarefied data set back to the trained model produced correct predictions of IBS subtype in 85% of the samples (151/178):

```
          C     D     M    |
    C    73    14     5    |  73
    D     5    64     3    |  64
    M     0     0    14    |  14
    _____    +  ___
    Correctly  predicted   | 151
```

The model was also trained with a dataset having an additional group of 626 control samples (non-IBS individuals). In this case, the model correctly assigned 98% of rarefied data to the correct group.

|          | C  | D  | M  | Controls |
|----------|----|----|----|----------|
| C        | 75 | 0  | 0  | 0        |
| D        | 0  | 77 | 0  | 0        |
| M        | 0  | 0  | 16 | 0        |
| Controls | 4  | 2  | 6  | 626      |

These results demonstrated the applicability of 16S microbiome profiles for prediction of IBS types with an accuracy of up to 98%. This also indicated that there are bacterial signatures in the human microbiome which can be used as a biomarker of IBS subtype and other bacterial dysbioses in general.

Example 4 Bacterial Biomarkers for IBS Diagnosis and Subtyping

A list of bacterial species whose abundance were most different across the IBS subtypes and healthy individuals was generated, which can be used to diagnose and subtype IBS. This list was generated using the microbiome profiles from the groups of individuals described in Example 2: IBS-C, IBS-D, IBS-M, and healthy controls. Generalised linear modelling with empirical Bayesian methods were used to provide stable results given that the number of samples was small. The results were also tested and confirmed with other statistical methods including the Student's t-test and the two-sample Kolmogorov-Smirnov test.

Tables 4 and 5 below show the top 100 bacteria with the most differentiated abundance between the IBS groups and healthy controls.

TABLE 4

List of top 1 to 50 species of bacteria with most differentiated abundance between IBS groups and healthy controls
Species name Lachnospira pectinoschiza
Lactobacillus rhamnosus
Scardovia inopinata
Enterococcus casseliflavus
Lachnoclostridium symbiosum
Blautia hansenii
Citrobacter farmeri
Bacteroides salyersiae
Enterobacter ludwigii
Acholeplasma Parvum
Soleaferrea massiliensis
Roseburia intestinalis
Gemmiger formicilis
Sutterella wadsworthensis
Variovorax beronicumulans
Prevotella ouloruml
Anaerotruncus colihominis
Janibacter limosus
Eubacterium ramulus
Oscillibacter valericigenes
Ruminococcus bromii
Intestinimonas butyriciproducens
Oscillibacter valericigenes
Eubacterium desmolans
Blautia hydrogenotrophica
Roseburia intestinalis
Ruminococcus bromii
Prevotella copri
Fusicatenibacter saccharMJrans
Faecalibacterium prausnitzii
Burkholderia cepacia
Tyzzerella lactatifermentans
Akkermansia muciniphila
Eggerthella sinensisl
Acinetobacter pittii
Oscillibacter valericigenes
Blautia glucerasea
Blautia glucerasea
Eubacterium sulci
Butyrivibrio crossotus
Ruminococcus bromii
Christensenella minuta
Flavobacterium resistens
Soleaferrea massiliensis
Oscillibacter valericigenes
Eubacterium sp
Clostridium frigoris
Alistipes indistinctus
Papillibacter cinnamivorans
Desulfitobacterium frappieri

TABLE 5

List of top 51 to 100 species of bacteria with most differentiated abundance between IBS groups and healthy controls
Species name Fictibacillus arsenicus
Prevotella copri
Ureibacillus thermosphaericus
Fusicatenibacter saccharvorans
Bacteroides thetaiotaomicron
Faecalibacterium prausnitzii
Erysipelotrichaceae Erysipelatoclostridium
Burkholderia cepacia TABLE 5-continued List of top 51 to 100 species of bacteria with most differentiated
abundance between IBS groups and healthy controls
Species name Bacteroides stercoris
Clostridium bolteae
Papillibacter cinnamivorans
Desulfitobacterium frappieri
Clostridium frigoris
Eubacterium sp
Alistipes sp
Soleaferrea massiliensis
Ruminococcus bromii
Akermansia muciniphila
Alistipes indistinctus
Eubacterium callanderi
Mogibacterium neglectum
Christensenella minuta
Flavobacterium resistens
Eggerthella sinensis
Akkermansia Muciniphila
Blautia Glucerasea
Oscillibacter valericigenes
Lactobacillus japonicus
Blautia glucerasea
Faecalibacterium prausnitzii
Scardovia inopinata
Streptococcus parasanguinis
Lachnospira pectinoschiza
Roseburia faecis
Citrobacter farmeri
Bacteroides salyersiae
Enterobacter ludwgii
Enterococcus casseliflavus
Anoxystipes fissicatena
Blautia hydrogenotrophica
Ruminococcus bromii
Oscillibacter valericigenes
Anaerofilum pentosovorans
Ruminococcus bromii
Anaerotruncus colihominis
Bacteroides graminisolvens
Prevotella oulorum
Robinsoniella peoriensis
Acholeplasma parvum
Sutterella wadsworthensis Of the list of 100 species shown in Tables 4 and 5, there were 13 bacteria whose abundance was most informative for IBS subtype prediction:
1. *Christensenella minuta*
2. *Papillibacter cinnamivorans*
3. *Bilophila wadsworthia*
4. *Ruminococcus bromii*
5. *Soleaferrea massiliensis*
6. *Akkermansia muciniphila*
7. *Oscillibacter valericigenes*
8. *Desulfitobacterium frappieri*
9. *Anaerofilum pentosovorans*
10. *Lactobacillus japonicus*
11. *Catabacter hongkongensis*
12. *Clostridium sporosphaeroides*
13. *Faecalibacterium prausnitzii*

In some instances the IBS classification model was improved by measuring the total abundance at the genus level, as opposed to individual species, or combined data from phylum, genus and species level. A prediction model using a Random Forest algorithm was trained with the abundances of 365 genera from the IBS-C, IBS-D, IBS-M, and healthy individuals, obtained using the methods described in Example 1. This model was tested against the rarefied dataset of 31,000 reads per sample described in Example 3:

|  | C | D | M | Control |
|---|---|---|---|---|
| C | 73 | 0 | 1 | 0 |
| D | 0 | 74 | 0 | 0 |
| M | 0 | 0 | 14 | 0 |
| Control | 6 | 5 | 7 | 626 |

The genus level classification resulted in a prediction accuracy of approximately 97%, which indicated that the abundance of certain genera of bacteria in a sample could be used as a biomarker to diagnose and predict IBS subtype. Of the 365 genera that were tested in the experiment described above, there were 30 genera that were the most informative for predicting IBS subtype, shown in Table 6 below.

TABLE 6

30 most informative bacteria genus for discrimination IBS groups and general population with Random Forest model

| Top 30 the most informative genus used in RandomForest model | mean (D) | mean (M) | mean (C) | mean (pop) | C* | D* | M* | Population* | Mean Decrease Accuracy | Mean Decrease Gini |
|---|---|---|---|---|---|---|---|---|---|---|
| Firmicutes_Clostridia_Clostridiales_Clostridiaceae_Alkaliphilus | 0.11% | 0.20% | 0.13% | 0.74% | 8.85 | 9.05 | 1.53 | 10.38 | 12.62 | 10.85 |
| Proteobacteria_Alphaproteobacteria_Sphingomonadales_Sphingomonadaceae_Sphingomonas | 0.00% | 0.00% | 0.00% | 0.01% | 6.05 | 8.87 | −0.36 | 10.97 | 12.39 | 7.78 |
| Firmicutes_Clostridia_Clostridiales_Peptococcaceae_Pelotomaculum | 0.07% | 0.08% | 0.07% | 0.53% | 7.72 | 7.09 | −0.79 | 6.89 | 9.81 | 7.41 |
| Actinobacteria_Actinobacteria_Coriobacteriales_Coriobacteriaceae_Eggerthella | 0.03% | 0.04% | 0.06% | 0.29% | 6.71 | 6.6 | 1.48 | 6.64 | 9.75 | 6.22 |
| Firmicutes_Erysipelotrichi_Erysipelotrichales_Erysipelotrichaceae_Eubacterium | 0.006% | 0.008% | 0.008% | 0.045% | 2.18 | 5.89 | 2.08 | 9.06 | 9.63 | 5.38 |
| Proteobacteria_Alphaproteobacteria_Rhodobacterales_Rhodobacteraceae_Paracoccus | 0.001% | 0.001% | 0.001% | 0.005% | 3.73 | 5.72 | 1.63 | 8 | 9.06 | 5.2 |
| Firmicutes_Clostridia_Clostridiales_Lachnospiraceae_Lachnoclostridium | 1.83% | 1.69% | 1.69% | 0.71% | 6.23 | 3.78 | 0.69 | 8.72 | 9 | 6.13 |
| Firmicutes_Bacilli_Bacillales_Bacillaceae_Bacillus | 0.02% | 0.01% | 0.01% | 0.05% | 4.75 | 0.11 | 0.63 | 8.79 | 8.93 | 4.4 |

TABLE 6-continued 30 most informative bacteria genus for discrimination IBS groups and general population with Random Forest model

| Top 30 the most informative genus used in RandomForest model | mean (D) | mean (M) | mean (C) | mean (pop) | C* | D* | M* | Population* | Mean Decrease Accuracy | Mean Decrease Gini |
|---|---|---|---|---|---|---|---|---|---|---|
| Firmicutes_Erysipelotrichia_Erysipelotrichales_Erysipelotrichaceae_Anaerorhabdus | 0.0017% | 0.0020% | 0.0022% | 0.0103% | 5.41 | 6.09 | 2.59 | 6.07 | 8.81 | 6.27 |
| Actinobacteria_Actinobacteria_Actinomycetales_Actinomycetaceae_Actinomyces | 0.016% | 0.019% | 0.022% | 0.054% | 2.48 | 3.77 | 2.15 | 6.95 | 8.25 | 4.45 |
| Proteobacteria_Alphaproteobacteria_Rhizobiales_Methylobacteriaceae_Methylobacterium | 0.001% | 0.001% | 0.001% | 0.006% | 6.19 | 4.64 | 2.95 | 6.88 | 8.17 | 4.71 |
| Proteobacteria_Gammaproteobacteria_Pseudomonadales_Pseudomonadaceae_Pseudomonas | 0.003% | 0.006% | 0.005% | 0.067% | 5.17 | 2.88 | 0.26 | 6.81 | 8.13 | 2.82 |
| Firmicutes_Bacilli_Lactobacillales_Streptococcaceae_Streptococcus | 0.16% | 0.26% | 0.15% | 0.96% | 4.65 | 2.25 | 0.59 | 6.73 | 8.09 | 4.64 |
| Firmicutes_Bacilli_Bacillales_Staphylococcaceae_Staphylococcus | 0.02% | 0.01% | 0.01% | 0.04% | 6.73 | 1.96 | −1.19 | 7.23 | 8.02 | 5.93 |
| Firmicutes_Clostridia_Clostridiales_Peptostreptococcaceae_Peptoclostridium | 0.00% | 0.00% | 0.00% | 0.03% | 4.41 | 3.69 | 2.29 | 5.61 | 7.29 | 4.05 |
| Firmicutes_Erysipelotrichia_Erysipelotrichales_Erysipelotrichaceae_Erysipelatoclostridium | 0.14% | 0.09% | 0.16% | 0.69% | 4.11 | 1.7 | 2.15 | 5.45 | 6.94 | 3.9 |
| Firmicutes_Clostridia_Clostridiales_Lachnospiraceae_Anaerostipes | 0.77% | 0.99% | 0.75% | 3.40% | 4.5 | 5.07 | −1.13 | 5.07 | 6.63 | 3.74 |
| Proteobacteria_Betaproteobacteria_Burkholderiales_Sutterellaceae_Sutterella | 0.91% | 0.78% | 0.53% | 0.12% | 0.83 | −0.03 | 2.02 | 6.82 | 6.47 | 2.23 |
| Proteobacteria_Alphaproteobacteria_Caulobacterales_Caulobacteraceae_Brevundimonas | 0.000% | 0.000% | 0.000% | 0.002% | 5.15 | 5.9 | 2.54 | 4.09 | 6.37 | 2.81 |
| Firmicutes_Clostridia_Clostridiales_Peptostreptococcaceae_Clostridium | 0.08% | 0.07% | 0.08% | 0.73% | 2.91 | 5.48 | −0.93 | 4.4 | 6.33 | 3.07 |
| Firmicutes_Clostridia_Clostridiales_Peptostreptococcaceae_Peptostreptococcaceae | 0.03% | 0.04% | 0.03% | 0.10% | 3.44 | 3.35 | −0.81 | 5.23 | 6.25 | 3.71 |
| Firmicutes_Clostridia_Coriobacteriales_Coriobacteriaceae_Slackia | 0.03% | 0.04% | 0.04% | 0.18% | 1.42 | 5.09 | 2.23 | 3.5 | 5.97 | 3.69 |
| Proteobacteria_Alphaproteobacteria_Sphingomonadales_Sphingomonadaceae_Blastomonas | 0.0007% | 0.0008% | 0.0010% | 0.0041% | 1.89 | 5.53 | 1.03 | 4.77 | 5.93 | 3.23 |
| Firmicutes_Bacilli_Lactobacillales_Lactobacillaceae_Lactobacillus | 0.41% | 0.48% | 0.62% | 1.12% | 0.92 | 2.79 | 1.94 | 4.9 | 5.32 | 1.65 |
| Actinobacteria_Actinobacteria_Coriobacteriales_Coriobacteriaceae_unclassified | 0.04% | 0.05% | 0.06% | 0.35% | 0.31 | 4.27 | 1.72 | 3.32 | 5.02 | 2.17 |
| Firmicutes_Clostridia_Clostridiales_Eubacteriaceae_Eubacterium | 3.23% | 3.41% | 3.58% | 7.01% | −0.23 | 3.58 | 1 | 5.49 | 5.01 | 2.98 |
| Proteobacteria_Gammaproteobacteria_Enterobacteriales_Enterobacteriaceae_Klebsiella | 0.05% | 0.13% | 0.03% | 0.20% | 0.53 | 1.34 | 0.91 | 4.99 | 4.62 | 1.97 |
| Proteobacteria_Alphaproteobacteria_Rhizobiales_Rhizobiaceae_Agrobacterium | 0.0004% | 0.0010% | 0.0009% | 0.0023% | 0.04 | 4.64 | −0.87 | 3.09 | 4.61 | 1.13 |
| Firmicutes_Clostridia_Clostridiales_Peptostreptococcaceae_unclassified | 0.16% | 0.13% | 0.18% | 1.35% | 4.38 | 3.91 | 0.33 | 2.51 | 4.42 | 2.94 |
| Proteobacteria_Alphaproteobacteria_Rhizobiales_Phyllobacteriaceae_Phyllobacterium | 0.001% | 0.002% | 0.003% | 0.005% | −1.68 | 3.34 | −0.37 | 4.16 | 4.42 | 1.54 |

Mean (D), (M), (C), (pop) = mean relative abundance in each group. C*, D*, M* = importance coefficient (higher represents greater prediction accuracy). Mean Decrease Accuracy and Mean Decrease Gini are discrimination coefficients which indicate the species' overall contribution to prediction accuracy.

Example 5 Diagnosis of Autism

Faecal samples were obtained from 118 non-autism individuals and 48 individuals with autism. The samples were processed as described in Example 2, the DNA was sequenced using the MiSeq (Illumina) instrument, and the resulting data was analysed using the pipeline described in Example 1. A Random Forest model was then trained on the microbiome profiles (at both species and genus level abundance) obtained from the non-autism and autism individuals. The model, using default settings and species level abundance, predicted Autism correctly for nearly all individuals except two individuals with autism, who were misclassified to the non-autism group, resulting in an error rate in range of 0.6-1%. The genus level abundance test gave similar results:

| Genus classification level (365 bacterial genera) Autism | | | Species classification level (2,009 bacterial species) Autism | | |
|---|---|---|---|---|---|
| | no | yes | | no | yes |
| no | 118 | 1 | no | 118 | 2 |
| yes | 0 | 47 | yes | 0 | 46 |

These results demonstrate the significance of the intestinal microbiome in the diagnosis of Autism. Therefore, the data was further analysed to determine the genera of bacteria whose abundance was most informative of whether or not an individual has autism. These genera are listed in Table 7 below.

TABLE 7

The most informative genera used in the Random Forest model for predicting Autism

| Top 40 the most informative genus used in RandomForest model in IBS samples with and without Autism | Mean abundance (Autism) | Mean abundance (NonAutism) | Autism* | Non Autism * | Mean Decrease Accuracy | Mean Decrease Gini |
|---|---|---|---|---|---|---|
| Firmicutes_Clostridia_Clostridiales_Ruminococcaceae_Ruminiclostridium | 2.3780% | 0.5394% | 4.45 | 4.34 | 5.36 | 1.04 |
| Firmicutes_Clostridia_Clostridiales_Clostridiaceae_Sarcina | 0.1551% | 0.0533% | 3.04 | 2.67 | 3.54 | 1.02 |
| Firmicutes_Clostridia_Clostridiales_Lachnospiraceae_Lachnoclostridium | 1.2762% | 1.8926% | 1.13 | 3.47 | 3.36 | 0.84 |
| Firmicutes_Clostridia_Clostridiales_Peptostreptococcaceae_Asaccharospora | 0.0263% | 0.0265% | 1.19 | 2.37 | 2.54 | 0.82 |
| Firmicutes_Clostridia_Clostridiales_Lachnospiraceae_Lachnobacterium | 0.0263% | 0.0324% | 1.72 | 2.17 | 2.53 | 0.53 |
| Firmicutes_Clostridia_Clostridiales_Lachnospiraceae_Anaerostipes | 0.5649% | 0.8357% | 0.89 | 2.21 | 2.42 | 0.57 |
| Firmicutes_Clostridia_Clostridiales_Ruminococcaceae_Faecalibacterium | 8.0944% | 10.7975% | 2.84 | 1.22 | 2.34 | 0.68 |
| Bacteroidetes_Bacteroidia_Bacteroidales_Bacteroidaceae_Bacteroides | 21.2738% | 19.7305% | 1.25 | 2.11 | 2.26 | 0.52 |
| Firmicutes_Clostridia_Clostridiales_Clostridiaceae_Mogibacterium | 0.0168% | 0.0408% | 1.43 | 2.21 | 2.26 | 0.27 |
| Proteobacteria_Gammaproteobacteria_Pasteurellales_Pasteurellaceae_Haemophilus | 0.0267% | 0.0468% | −0.71 | 2.49 | 2.22 | 0.32 |
| Firmicutes_Clostridia_Clostridiales_Peptostreptococcaceae_Intestinibacter | 0.0003% | 0.0003% | 2.03 | 1.32 | 2 | 0.1 |
| Actinobacteria_Actinobacteria_Actinomycetales_Actinomycetaceae_Mobiluncus | 0.0010% | 0.0016% | 1.43 | 1.99 | 1.94 | 0.05 |
| Firmicutes_Bacilli_Lactobacillales_Lactobacillaceae_Lactobacillus | 0.7177% | 0.4302% | 2.21 | 0.56 | 1.89 | 1.05 |
| Bacteroidetes_Bacteroidia_Bacteroidales_Rikenellaceae_Alistipes | 1.8353% | 2.8529% | 0.58 | 1.9 | 1.88 | 0.56 |
| Firmicutes_Clostridia_Clostridiales_Lachnospiraceae_Dorea | 0.7551% | 0.9481% | −0.52 | 2.43 | 1.83 | 0.37 |
| Actinobacteria_Actinobacteria_Coriobacteriales_Coriobacteriaceae_unclassified | 0.0303% | 0.0595% | 0.66 | 1.67 | 1.81 | 0.56 |
| Proteobacteria_Gammaproteobacteria_Alteromonadales_Ferrimonadaceae_Ferrimonas | 0.0148% | 0.0251% | 2.01 | 1.08 | 1.8 | 0.36 |
| Firmicutes_Clostridia_Clostridiales_Peptostreptococcaceae_Romboutsia | 0.1183% | 0.1296% | 0.91 | 1.55 | 1.76 | 0.72 |
| Proteobacteria_Gammaproteobacteria_Pasteurellales_Pasteurellaceae_Actinobacillus | 0.0036% | 0.0040% | 1.54 | 1.45 | 1.74 | 0.11 |
| Firmicutes_Clostridia_Clostridiales_Ruminococcaceae_Anaerofilum | 0.0179% | 0.0309% | 0.46 | 1.94 | 1.71 | 0.39 |
| Proteobacteria_Gammaproteobacteria_Enterobacteriales_Enterobacteriaceae_Erwinia | 0.0119% | 0.0174% | 0.95 | 1.28 | 1.67 | 0.21 |
| Firmicutes_Clostridia_Clostridiales_Veillonellaceae_Phascolarctobacterium | 0.0230% | 0.0271% | −0.73 | 2.42 | 1.61 | 0.15 |
| Firmicutes_Clostridia_Clostridiales_Veillonellaceae_Selenomonas | 0.0080% | 0.0995% | 0.69 | 1.49 | 1.54 | 0.28 |
| Actinobacteria_Actinobacteria_Actinomycetales_Microbacteriaceae_Microbacterium | 0.0062% | 0.0064% | 1.57 | 0.83 | 1.51 | 0.15 |
| Firmicutes_Bacilli_Bacillales_Planococcaceae_Ureibacillus | 0.0027% | 0.0192% | −0.08 | 1.81 | 1.51 | 0.12 |
| Proteobacteria_Gammaproteobacteria_Enterobacteriales_Enterobacteriaceae_Proteus | 0.0004% | 0.0016% | 0.79 | 0.85 | 1.49 | 0.06 |
| Firmicutes_Clostridia_Clostridiales_Veillonellaceae_Megamonas | 0.3696% | 0.4829% | 1.09 | 1.29 | 1.46 | 0.4 |
| Firmicutes_Clostridia_Clostridiales_Christensenellaceae_Christensenella | 0.0579% | 0.1054% | −0.16 | 2.31 | 1.44 | 0.35 |
| Bacteroidetes_Bacteroidia_Bacteroidales_Odoribacteraceae_Butyricimonas | 0.0562% | 0.0455% | −0.34 | 1.8 | 1.42 | 0.53 |
| Proteobacteria_Epsilonproteobacteria_Campylobacterales_Campylobacteraceae_Arcobacter | 0.0000% | 0.0002% | 0 | 1.41 | 1.42 | 0.03 |
| Proteobacteria_Gammaproteobacteria_Enterobacteriales_Enterobacteriaceae_Yersinia | 0.0002% | 0.0014% | 0 | 1.41 | 1.42 | 0.03 |

TABLE 7-continued

The most informative genera used in the Random Forest model for predicting Autism

| Top 40 the most informative genus used in RandomForest model in IBS samples with and without Autism | Mean abundance (Autism) | Mean abundance (NonAutism) | Autism* | Non Autism * | Mean Decrease Accuracy | Mean Decrease Gini |
|---|---|---|---|---|---|---|
| Firmicutes_Clostridia_Clostridiales_Lachnospiraceae_Lachnoanaerobaculum | 0.0004% | 0.0009% | 1 | 0.6 | 1.42 | 0.02 |
| Proteobacteria_Betaproteobacteria_Burkholderiales_Comamonadaceae_Variovorax | 0.0002% | 0.0016% | −0.38 | 1.68 | 1.39 | 0.12 |
| Proteobacteria_Gammaproteobacteria_Enterobacteriales_Enterobacteriaceae_Citrobacter | 0.0132% | 0.0201% | 0.93 | 1.33 | 1.37 | 0.17 |
| Firmicutes_Bacilli_Bacillales_Paenibacillaceae_Paenibacillus | 0.0018% | 0.0109% | −0.43 | 1.99 | 1.37 | 0.1 |
| Tenericutes_Mollicutes_Anaeroplasmatales_Anaeroplasmataceae_Anaeroplasma | 0.0010% | 0.0013% | 0 | 1.38 | 1.35 | 0.09 |
| Firmicutes_Bacilli_Bacillales_Bacillaceae_Fictibacillus | 0.0002% | 0.0009% | 1 | 1 | 1.35 | 0.01 |
| Firmicutes_Clostridia_Clostridiales_Lachnospiraceae_Eisenbergiella | 0.0196% | 0.0166% | 0.63 | 1.12 | 1.29 | 0.19 |
| Proteobacteria_Betaproteobacteria_Burkholderiales_Burkholderiaceae_Lautropia | 0.0117% | 0.0382% | −0.26 | 1.69 | 1.28 | 0.15 |
| Firmicutes_Clostridia_Clostridiales_Unclassified_Clostridiales_Howardella | 0.0001% | 0.0001% | 1.42 | 0.75 | 1.27 | 0.06 |

Mean abundance = mean relative abundance in each group. Autism* and Non-Autism* = importance coefficient (higher represents greater prediction accuracy).
Mean Decrease Accuracy and Mean Decrease Gini are are discrimination coefficients which indicate the species' overall contribution to prediction accuracy . . .

Example 6 Diagnosis of Intestinal Senescence

The same approach that was used for the prediction IBS subtypes was also used for the prediction of age and intestinal senescence in an unknown sample. It is known that age is one of the major factors affecting the microbiome composition in human gut. It changes rapidly in first few years of life (0-3 years, "baby") then reaches maturity during the age 4-12 ("child") and then relatively stable through "adult" life (13-59 years) after which the composition becomes different from the rest of the population (60+, "senior"). The age margins utilised are not firmly confirmed nevertheless the Random Forest algorithm was trained on microbiome profiles from faecal samples of a population of individuals with varying age. This dataset comprised 456 "Adults", 35 "Babies", 59 "Children", and 76 "Seniors". The model correctly predicted 100% of Adult group in non-rarefied samples using genus and species level abundance. The smaller age groups in "Baby", "Child", and "Senior" were not predicted with the same level of accuracy:

| | Genus classification level (365 bacterial genus) | | | | | Species classification level (2,009 bacterial species) | | | |
|---|---|---|---|---|---|---|---|---|---|
| | Adult | Baby | Child | Senior | | Adult | Baby | Child | Senior |
| Adult | 456 | 12 | 30 | 45 | Adult | 456 | 11 | 32 | 48 |
| Baby | 0 | 23 | 0 | 0 | Baby | 0 | 24 | 0 | 0 |
| Child | 0 | 0 | 29 | 0 | Child | 0 | 0 | 27 | 0 |
| Senior | 0 | 0 | 0 | 31 | Senior | 0 | 0 | 0 | 28 |

In both the species level and genus level models the misclassification in those groups was about 50%. Modelling using genus level taxonomy showed slightly better performance compare to the species for age prediction. The prediction model could be improved by balancing the number of individuals in each age group.

Example 7 Diagnosis of IBS—Genus Level

The methods described in Example 1 were used to identify the genera of bacteria whose abundance was most indicative of whether or not a subject has IBS.

Both a Random Forest and a limma algorithm used to identify the most indicative genera of bacteria, the results are shown in Tables 8 to 11.

TABLE 8

Top 50 most indicative bacterial genera for determining whether a subject has IBS (Random Forest)

| Bacteria genus | Mean relative abundance Non-IBS | Mean relative abundance IBS |
|---|---|---|
| Corynebacterium | 0.096% | 0.041% |
| Lachnobacterium | 0.081% | 0.029% |
| Propionibacterium | 0.040% | 0.014% |

TABLE 8-continued

Top 50 most indicative bacterial genera for determining whether a subject has IBS (Random Forest)

| Bacteria genus | Mean relative abundance Non-IBS | Mean relative abundance IBS |
|---|---|---|
| Kytococcus | 0.022% | 0.004% |
| Fusobacterium | 0.132% | 0.077% |
| Veillonella | 0.049% | 0.013% |
| Prevotella | 22.241% | 6.083% |
| Anaerofustis | 0.035% | 0.010% |
| Arthrobacter | 0.139% | 0.070% |
| Dysgonomonas | 0.027% | 0.013% |
| Calothrix | 0.028% | 0.018% |
| Atopobium | 0.241% | 0.073% |
| Brevibacterium | 0.029% | 0.011% |
| Micrococcus | 0.041% | 0.011% |
| Burkholderia | 0.086% | 0.003% |
| Veillonella | 0.156% | 0.037% |
| Pelotomaculum | 0.132% | 0.067% |
| Acidaminococcus | 0.055% | 0.019% |
| Mitsuokella | 0.024% | 0.005% |
| Allisonella | 0.061% | 0.004% |
| Bifidobacterium | 0.238% | 0.357% |
| Paraprevotella | 0.067% | 0.222% |
| unclassified | 0.200% | 0.024% |
| Selenomonas | 0.006% | 0.000% |
| unclassified | 0.121% | 0.049% |
| Peptostreptococcaceae | 0.047% | 0.031% |
| Enorma | 0.010% | 0.004% |
| Slackia | 0.058% | 0.035% |
| Eubacterium | 0.020% | 0.004% |
| Actinobacillus | 0.006% | 0.001% |
| unclassified | 0.967% | 2.175% |
| Atopobium | 0.030% | 0.015% |
| Alistipes | 1.062% | 2.630% |
| Collinsella | 0.079% | 0.023% |
| Microbacterium | 0.006% | 0.001% |
| Gemmiger | 0.861% | 1.407% |
| Curtobacterium | 0.606% | 0.456% |
| Negativicoccus | 0.111% | 0.020% |
| Odoribacter | 0.082% | 0.219% |
| Eubacterium | 0.388% | 0.078% |
| unclassified | 0.301% | 0.195% |
| .Ruminococcus. | 0.156% | 0.274% |
| Collinsella | 0.774% | 0.503% |
| Megamonas | 0.760% | 0.560% |
| Roseburia | 4.321% | 3.049% |
| Erysipelatoclostridium | 0.092% | 0.141% |
| Peptoniphilus | 0.443% | 0.836% |
| Blautia | 0.396% | 0.224% |
| Carnobacterium | 0.060% | 0.006% |
| Cellulosilyticum | 0.023% | 0.024% |

TABLE 9

Random Forest classification error rate for determining whether a subject has IBS (genera)

| Number of genera used for classification | IBS | Non-IBS | Overall |
|---|---|---|---|
| Top 100 | 0.6% | 18.2% | 5.84% |
| Top 50 | 0.6% | 19.5% | 6.23% |
| Top 30 | 0.6% | 18.2% | 5.84% |
| Top 15 | 1.1% | 20.8% | 7.00% |
| Top 5 | 3.3% | 16.9% | 7.39% |

TABLE 10

Top 50 most indicative bacterial genera for determining whether a subject has IBS (limma)

| Bacteria genus | Mean relative abundance Non-IBS | Mean relative abundance IBS |
|---|---|---|
| Corynebacterium | 0.096% | 0.041% |
| Lachnobacterium | 0.081% | 0.029% |
| Arthrobacter | 0.139% | 0.070% |
| Fusobacterium | 0.132% | 0.077% |
| Prevotella | 22.241% | 6.083% |
| Atopobium | 0.241% | 0.073% |
| Propionibacterium | 0.040% | 0.014% |
| Anaerofustis | 0.035% | 0.010% |
| Pelotomaculum | 0.132% | 0.067% |
| Odoribacter | 0.082% | 0.219% |
| Veillonella | 0.156% | 0.037% |
| Bacteroides | 13.431% | 20.759% |
| Brevibacterium | 0.029% | 0.011% |
| Coprobacter | 0.040% | 0.069% |
| Alistipes | 1.062% | 2.630% |
| .Ruminococcus. | 0.156% | 0.274% |
| Ferrionas | 0.013% | 0.019% |
| Alkaliphilus | 0.176% | 0.132% |
| Lautropia | 0.008% | 0.035% |
| Veillonella | 0.049% | 0.013% |
| Enterococcus | 0.110% | 0.466% |
| Blautia | 0.396% | 0.224% |
| Pectinatus | 0.004% | 0.009% |
| Gemmiger | 0.861% | 1.407% |
| Micrococcus | 0.041% | 0.011% |
| Oxalobacter | 0.038% | 0.016% |
| Curtobacterium | 0.606% | 0.456% |
| Peptostreptococcaceae | 0.047% | 0.031% |
| Lachnoclostridium | 1.072% | 1.756% |
| Ruminiclostridium | 0.286% | 1.075% |
| Parasutterella | 0.204% | 0.397% |
| Cetobacterium | 0.054% | 0.105% |
| Tolumonas | 0.017% | 0.029% |
| unclassified | 0.121% | 0.049% |
| unclassified | 0.609% | 0.129% |
| Burkholderia | 0.086% | 0.003% |
| Anaerostipes | 0.510% | 0.793% |
| Oribacterium | 0.277% | 0.201% |
| Eubacterium | 0.388% | 0.078% |
| Roseburia | 4.321% | 3.049% |
| unclassified | 0.041% | 0.213% |
| unclassified | 0.967% | 2.175% |
| Collinsella | 0.774% | 0.503% |
| Peptococcus | 0.353% | 0.224% |
| Flavobacterium | 0.833% | 1.448% |
| Kytococcus | 0.022% | 0.004% |
| Selenomonas | 0.008% | 0.066% |
| Atopobium | 0.030% | 0.015% |
| Enorma | 0.010% | 0.004% |
| Capnocytophaga | 0.010% | 0.008% |

TABLE 11

Limma classification error rate for determining whether a subject has IBS (genera)

| Number of genera used for classification | IBS | Non-IBS | Overall |
|---|---|---|---|
| Top 100 | 0.6% | 20.8% | 6.61% |
| Top 50 | 1.1% | 19.5% | 6.61% |
| Top 30 | 0.6% | 19.5% | 6.23% |
| Top 15 | 1.1% | 14.3% | 5.06% |
| Top 5 | 4.4% | 15.6% | 7.78% |

There is a significant overlap between the genera identified using the Random Forest and limma algorithms. From assessment of the results of both algorithms, the following list of bacteria were identified as those whose abundance was most indicative of whether or not a subject had IBS:

*Corynebacterium, Lachnobacterium, Propionibacterium, Kytococcus, Fusobacterium, Veillonella, Prevotella, Anaerofustis, Arthrobacter, Dysgonomonas, Calothrix, Atopobium, Brevibacterium, Micrococcus, Burkholderia, Veillonella, Pelotomaculum, Acidaminococcus, Mitsuokella, Allisonella, Odoribacter, Bacteroides, Coprobacter, Alistipes, Ruminococcus, Ferrimonas, Alkaliphilus,* and *Lautropia.*

Tables 9 and 11 show that when only the top 5 genera were used, the overall classification error rate was in the range of 7% to 8%, depending on the algorithm used. These results demonstrate that the abundance of as few as 5 genera of bacteria can be used to successfully diagnose a subject with IBS, with an accuracy of approximately 92% to 93%.

Example 8 Diagnosis of IBS—Species Level

The methods described in Example 1 were used to identify the species of bacteria whose abundance was most indicative of whether or not a subject has IBS.

Both a Random Forest and a limma algorithm used to identify the most indicative species of bacteria, the results are shown in Tables 12 to 15.

TABLE 12

Top 50 most indicative bacterial species for determining whether a subject has IBS (Random Forest)

| Bacteria species name | Mean relative abundance Non-IBS | Mean relative abundance IBS |
|---|---|---|
| SmartDNA0056.Corynebacterium_minutissimum.SD18931 | 0.0595% | 0.0212% |
| OTU687.NN.Prevotella_oulora_PVORR16SH.D.91.7 | 0.3080% | 0.0616% |
| Fusobacterium_naviforme | 0.1282% | 0.0551% |
| Prevotella_ruminicola | 0.2768% | 0.0990% |
| Bifidobacterium_thermacidophilum | 0.1343% | 0.0716% |
| SmartDNA0193.Dysgonomonas_wimpennyi.SD18556 | 0.0246% | 0.0056% |
| Propionibacterium_acnes | 0.0383% | 0.0123% |
| Corynebacterium_tuberculostearicum | 0.0260% | 0.0075% |
| Brevibacterium_casei | 0.0130% | 0.0017% |
| Lachnobacterium_bovis | 0.0821% | 0.0297% |
| SmartDNA0245.Prevotella_dentasini.SD18921 | 0.5118% | 0.0356% |
| Prevotella_albensis | 0.0813% | 0.0143% |
| OTU1482.NN.Veillonella_atypica_X84007.D.96.9 | 0.0454% | 0.0110% |
| Kytococcus_schroeteri | 0.0221% | 0.0036% |
| OTU1373.NN.Prevotella_copri_AB064923.D.88.2 | 1.2165% | 0.1460% |
| SmartDNA0045.Bacteroides_barnesiae.SD18764 | 0.0329% | 0.0463% |
| OTU234.NN.Prevotella_conceptionensis_HM587326.D.87.4 | 0.0249% | 0.0288% |
| SmartDNA0043.Anaerofustis_stercorihominis.SD18894 | 0.0349% | 0.0097% |
| Bifidobacterium_thermophilum | 0.0072% | 0.0004% |
| Prevotella_brevis | 0.0156% | 0.0020% |
| SmartDNA0099.Prevotella_stercorea.SD18922 | 1.3756% | 0.3258% |
| OTU1112.NN.Prevotella_copri_AB064923.D.94.8 | 0.9109% | 0.1466% |
| OTU150.NN.Barnesiella_intestinihominis_AB370251.D.85.8 | 0.0257% | 0.0517% |
| SmartDNA0133.Arthrobacter_creatinolyticus.SD16598 | 0.1379% | 0.0692% |
| Anaerostipes_rhamnosus | 0.0584% | 0.0381% |
| Prevotella_copri | 4.1703% | 1.0524% |
| SmartDNA0051.Calothrix_parietina.SD18926 | 0.0283% | 0.0181% |
| OTU497.NN.Prevotella_copri_AB064923.D.94.1 | 1.3216% | 0.1730% |
| OTU665.NN.Prevotella_copri_AB064923.D.96.6 | 0.3509% | 0.0606% |
| SmartDNA0019.Veillonella_sp.SD18935 | 0.0325% | 0.0018% |
| OTU1173.NN.Roseburia_faecis_AY804149.D.94.9 | 0.0181% | 0.0080% |
| SmartDNA0134.Atopobium_fossor.SD18741 | 0.2441% | 0.0744% |
| SmartDNA0092.Mitsuokella_multacida.SD18780 | 0.0240% | 0.0052% |
| Bifidobacterium_pseudocatenulatum | 0.0247% | 0.0102% |
| SmartDNA0234.Paraprevotella_xylaniphila.SD18374 | 0.0674% | 0.2248% |
| SmartDNA0034.Micrococcus_luteus.SD18041 | 0.0292% | 0.0071% |
| Prevotella_oulora | 0.1199% | 0.0258% |
| OTU551.NN.Prevotella_copri_AB064923.D.96.9 | 1.5196% | 0.2225% |
| SmartDNA0096.Pelotomaculum_isophthalicicum.SD18676 | 0.1339% | 0.0679% |
| OTU306.NN.Barnesiella_intestinihominis_AB370251.D.85.7 | 0.1493% | 0.0923% |
| OTU1268.NN.Prevotella_copri_AB064923.D.96.5 | 3.0708% | 0.7815% |
| OTU1275.NN.Prevotella_copri_AB064923.D.96.9 | 0.6401% | 0.1361% |
| OTU944.NN.Intestinimonas_butyriciproducens_JX101685.1.D.91.5 | 0.0373% | 0.0152% |
| OTU1290.NN.Clostridium_lactatifermentans_AY033434.D.92.7 | 0.0174% | 0.0067% |
| OTU314.NN.Blautia_coccoides_EF025906.D.94.9 | 0.0109% | 0.0109% |
| OTU164.NN.Ruminococcus_bromii_DQ882649.D.85.6 | 0.0483% | 0.0335% |
| SmartDNA0033.Micrococcus_luteus.SD18041 | 0.0070% | 0.0005% |
| SmartDNA0166.Clostridium_autoethanogenum.SD18759 | 0.0183% | 0.0230% |
| SmartDNA0243.Prevotella_amnii.SD18918 | 0.2134% | 0.0476% |
| Selenomonas_ruminantium | 0.0063% | 0.0004% |

TABLE 13

Random Forest classification error rate for determining whether a subject has IBS (species)

| Number of species used for classification | IBS | Non-IBS | Overall |
|---|---|---|---|
| Top 100 | 0.6% | 11.7% | 3.89% |
| Top 50 | 0.6% | 10.4% | 3.50% |
| Top 30 | 1.1% | 10.3% | 3.89% |
| Top 15 | 0.5% | 10.3% | 3.50% |
| Top 5 | 1.1% | 10.3% | 3.89% |

TABLE 14

Top 50 most indicative bacterial species for determining whether a subject has IBS (limma)

| Bacteria genus | Mean relative abundance Non-IBS | Mean relative abundance IBS |
|---|---|---|
| Prevotella_ruminicola | 0.2768% | 0.0990% |
| Fusobacterium_naviforme | 0.1282% | 0.0551% |
| SmartDNA0056.Corynebacterium_minutissimum.SD18931 | 0.0595% | 0.0212% |
| Bifidobacterium_thermacidophilum | 0.1343% | 0.0716% |
| Lachnobacterium_bovis | 0.0821% | 0.0297% |
| OTU687.NN.Prevotella_oulora_PVORR16SH.D.91.7 | 0.3080% | 0.0616% |
| SmartDNA0133.Arthrobacter_creatinolyticus.SD16598 | 0.1379% | 0.0692% |
| SmartDNA0134.Atopobium_fossor.SD18741 | 0.2441% | 0.0744% |
| SmartDNA0247.Prevotella_paludivivens.SD18896 | 2.1909% | 0.5818% |
| Corynebacterium_tuberculostearicum | 0.0260% | 0.0075% |
| Propionibacterium_acnes | 0.0383% | 0.0123% |
| SmartDNA0096.Pelotomaculum_isophthalicicum.SD18676 | 0.1339% | 0.0679% |
| SmartDNA0043.Anaerofustis_stercorihominis.SD18894 | 0.0349% | 0.0097% |
| OTU1622.NN.Roseburia_intestinalis_AB661435.D.90.2 | 0.6564% | 0.3377% |
| OTU53.NN.Clostridium_symbiosum_CLORR16SAA.D.94.4 | 0.0337% | 0.0821% |
| OTU306.NN.Barnesiella_intestinihominis_AB370251.D.85.7 | 0.1493% | 0.0923% |
| SmartDNA0027.Bacteroides_fragilis.SD1840 | 0.0597% | 0.2838% |
| Anaerostipes_rhamnosus | 0.0584% | 0.0381% |
| SmartDNA0023.Collinsella_aerofaciens.SD18947 | 0.3023% | 0.1404% |
| OTU1327.NN.Clostridium_bolteae_AJ508452.D.93 | 0.0669% | 0.3085% |
| OTU513.NN.Blautia_glucerasea_AB588023.D.95.4 | 0.1063% | 0.1882% |
| Lachnoclostridium_bolteae | 0.0620% | 0.1936% |
| SmartDNA0042.Alkaliphilus_crotonatoxidans.SD18709 | 0.1589% | 0.1098% |
| SmartDNA0036.Bacteroides_uniformis.SD16737 | 0.3291% | 1.0763% |
| OTU543.NN.Gemmiger_formicilis_GU562446.D.96.7 | 0.0290% | 0.0721% |
| OTU913.NN.Eubacterium_rectale_AY804151.D.95.6 | 0.2805% | 0.1226% |
| OTU1048.NN.Clostridium_populeti_X71853.D.91.9 | 0.1311% | 0.0540% |
| SmartDNA0137.Bacteroides_fragilis.SD18704 | 0.0221% | 0.1928% |
| SmartDNA0242.Coprobacter_fastidiosus.SD18964 | 0.0403% | 0.0697% |
| SmartDNA0068.Ferrimonas_futtsuensis.SD18946 | 0.0127% | 0.0190% |
| OTU1628.NN.Papillibacter_cinnamivorans_AF167711.D.89 | 0.0048% | 0.0078% |
| OTU176.NN.Butyrivibrio_crossotus_FR733670.D.87.8 | 0.2231% | 0.2126% |
| SmartDNA0222.Lautropia_mirabilis.SD18900 | 0.0079% | 0.0356% |
| SmartDNA0200.Enterococcus_azikeevi.SD18929 | 0.1037% | 0.4689% |
| OTU228.NN.Sutterella_parvirubra_AB300989.D.92.9 | 0.0143% | 0.0339% |
| SmartDNA0205.Alistipes_putredinis.SD18818 | 0.3807% | 0.7498% |
| SmartDNA0206.Flavobacterium_cauense.SD18252 | 0.4437% | 1.0016% |
| OTU120.NN.Anoxystipes_fissicatena_NR_104800.1.D.92.1 | 0.0323% | 0.0474% |
| OTU1624.NN.Clostridium_sphenoides_X73449.D.97 | 0.0309% | 0.0572% |
| Bacteroides_finegoldii | 0.1172% | 0.3417% |
| OTU492.NN.Gemmiger_formicilis_GU562446.D.91.7 | 0.0299% | 0.0815% |
| OTU85.NN.Blautia.Ruminococcus._massiliensis_JN657221.2.D.90.9 | 0.4002% | 0.2277% |
| OTU407.NN.Soleaferrea_massiliensis_JX101688.D.87.4 | 0.0305% | 0.0921% |
| OTU1315.NN.Eubacterium_desmolans_EUBRRDO.D.94.2 | 0.0787% | 0.1156% |
| SmartDNA0235.Pectinatus_cerevisiiphilus.SD18672 | 0.0037% | 0.0087% |
| SmartDNA0141.Bacteroides_uniformis.SD17416 | 0.1186% | 0.1946% |
| OTU117.NN.Clostridium_bolteae_AJ508452.D.90.7 | 0.0679% | 0.2453% |
| SmartDNA0193.Dysgonomonas_wimpennyi.SD18556 | 0.0246% | 0.0056% |
| OTU1174.NN.Clostridium_glycyrrhizinilyticum_AB233029.D.93 | 0.0599% | 0.1296% |
| SmartDNA0011.Odoribacter_sp_HQ769639 | 0.0785% | 0.1306% |

TABLE 15

Limma classification error rate for determining
whether a subject has IBS (species)

| Number of species used for classification | IBS | Non-IBS | Overall |
|---|---|---|---|
| Top 100 | 0.0% | 11.7% | 3.50% |
| Top 50 | 0.6% | 10.4% | 3.50% |
| Top 30 | 0.6% | 10.4% | 3.50% |
| Top 15 | 0.6% | 11.7% | 3.89 |
| Top 5 | 3.3% | 13.0% | 6.23% |

There is a significant overlap between the species identified using the Random Forest and limma algorithms. From assessment of the results of both algorithms, the following bacterial species were identified as those whose abundance was most indicative of whether or not a subject had IBS: *Corynebacterium minutissimum, Prevotella oulora, Fusobacterium naviforme, Prevotella ruminicola, Bifidobacterium thermacidophilum, Dysgonomonas wimpennyi, Propionibacterium acnes, Corynebacterium tuberculostearicum, Brevibacterium casei, Lachnobacterium bovis, Prevotella dentasini, Prevotella albensis, Veillonella atypica, Kytococcus schroeteri, Prevotella copri, Bacteroides barnesiae, Prevotella conceptionensis, Anaerofustis stercorihominis, Bifidobacterium thermophilum, Prevotella brevis, Roseburia intestinalis, Clostridium symbiosum, Barnesiella intestinihominis, Bacteroides fragilis, Anaerostipes rhamnosus, Collinsella aerofaciens, Clostridium bolteae, Arthrobacter creatinolyticus, Atopobium fossor, Prevotella paludivivens,* and *Pelotomaculum isophthalicicum.*

Tables 13 and 15 show that when only the top 5 species were used, the overall classification error rate was in the range of 4% to 6%, depending on the algorithm used. These results demonstrate that the abundance of as few as 5 species of bacteria can be used to successfully diagnose a subject with IBS, with an accuracy of approximately 94% to 96%.

Example 9 Determining a Subtype of IBS in a Subject with IBS

The methods described in Example 1 were used to identify the species of bacteria whose abundance was most indicative of whether or not a subject with IBS had IBS-C (constipation) or IBS-D (diarrhoea).

Both a Random Forest and a limma algorithm used to identify the most indicative species of bacteria, the results are shown in Tables 16 to 19.

TABLE 16

Top 50 most indicative bacterial species for determining
whether a subject has IBS-C or IBS-D (Random Forest)

| Bacteria species name | Mean relative abundance IBS-C | Mean relative abundance IBS-D |
|---|---|---|
| OTU867.NN.Christensenella_minuta_AB490809.D.91.9 | 0.0484% | 0.0043% |
| OTU1119.NN.Soleaferrea_massiliensis_JX101688.D.89.3 | 0.1189% | 0.0230% |
| OTU662.NN.Papillibacter_cinnamivorans_AF167711.D.90.1 | 0.1874% | 0.0535% |
| OTU1682.NN.Oscillibacter_valericigenes_AB238598.D.91.1 | 0.7030% | 0.0535% |
| OTU222.NN.Ruminococcus_bromii_DQ882649.D.89.9 | 0.1091% | 0.0173% |
| OTU492.NN.Gemmiger_formicilis_GU562446.D.91.7 | 0.1925% | 0.0300% |
| Desulfitobacterium_frappieri | 0.0405% | 0.0086% |
| OTU131.NN.Oscillibacter_valericigenes_AB238598.D.93.5 | 0.3889% | 0.0740% |
| Alistipes_obesi | 0.1394% | 0.0133% |
| OTU363.NN.Anaerofilum_pentosovorans_X97852.D.92.9 | 0.0443% | 0.0082% |
| Akkermansia_muciniphila | 2.3882% | 0.1143% |
| Alkaliphilus_crotonatoxidans.NR_041892 | 0.0454% | 0.0013% |
| OTU482.NN.Eubacterium_sulci_AJ006963.D.89.4 | 0.0536% | 0.0119% |
| OTU693.NN.Christensenella_minuta_AB490809.D.86.6 | 0.7557% | 0.0081% |
| OTU428.NN.Christensenella_minuta_AB490809.D.84.9 | 0.0603% | 0.0013% |
| OTU397.NN.Oscillibacter_valericigenes_AB238598.D.86.1 | 0.5910% | 0.0066% |
| SmartDNA0145.Bdellovibrio_exovorus.SD18781 | 0.1550% | 0.0017% |
| OTU918.NN.Oscillibacter_valericigenes_AB238598.D.88.4 | 0.9842% | 0.2545% |
| SmartDNA0187.Curtobacterium_pusillum.SD18704 | 0.9904% | 0.0533% |
| OTU152.NN.Oscillibacter_valericigenes_AB238598D.94.3 | 1.2829% | 0.0943% |
| OTU58.NN.Oscillospira.Flavonifractor._plautii_Y18187D.95.5 | 0.1250% | 0.0409% |
| OTU1212.NN.Ruminococcus_lactaris_NR_027579.1.D.87.5 | 0.2500% | 0.0637% |
| SmartDNA0252.Akkermansia_muciniphila.SD18896 | 0.5138% | 0.0318% |
| OTU776.NN.Oscillospira.Flavonifractor._plautii_Y18187.D.93.4 | 0.1284% | 0.0601% |
| OTU929.NN.Christensenella_minuta_AB490809.D.86.2 | 0.0536% | 0.0000% |
| SmartDNA0226.Mogibacterium_neglectum.SD18573 | 0.0635% | 0.0172% |
| OTU1488.NN.Roseburia_inulinivorans_AJ270474.D.90 | 0.0427% | 0.0120% |
| SmartDNA0155.Butyricimonas_virosa.SD18962 | 0.0693% | 0.0242% |
| OTU1534.NN.Oscillospira.Flavonifractor._plautii_Y18187.D.95.4 | 0.0893% | 0.0597% |
| OTU933.NN.Intestinimonas_butyriciproducens_JX101685.1.D.87.4 | 0.0637% | 0.0036% |
| OTU353.NN.Oscillibacter_valericigenes_AB238598.D.93.8 | 0.4395% | 0.1062% |
| Alistipes_indistinctus | 0.0699% | 0.0083% |
| OTU605.NN.Oscillibacter_valericigenes_AB238598.D.93.9 | 0.6123% | 0.0642% |
| OTU1024.Ruminiclostridium_clariflavum.NR_102987 | 0.1628% | 0.0092% |
| OTU1051.NN.Christensenella_minuta_AB490809.D.87.2 | 0.0171% | 0.0008% |
| SmartDNA0148.Bilophila_wadsworthia.SD18626 | 0.1341% | 0.0788% |
| OTU997.NN.Catabacter_hongkongensis_AB671763.D.82.9 | 0.0405% | 0.0100% |
| OTU164.NN.Ruminococcus_bromii_DQ882649.D.85.6 | 0.0544% | 0.0134% |
| SmartDNA0166.Clostridium_autoethanogenum.SD18759 | 0.0542% | 0.0016% |
| OTU1354.NN.Papillibacter_cinnamivorans_AF167711.D.86.3 | 0.2249% | 0.0022% |
| OTU804.NN.Oscillibacter_valericigenes_AB238598.D.89.7 | 0.0192% | 0.0008% |
| OTU857.NN.Eubacterium_sulci_AJ006963.D.90.2 | 0.0151% | 0.0028% |

TABLE 16-continued

Top 50 most indicative bacterial species for determining
whether a subject has IBS-C or IBS-D (Random Forest)

| Bacteria species name | Mean relative abundance IBS-C | Mean relative abundance IBS-D |
|---|---|---|
| OTU1248.NN.Oscillospira.Flavonifractor._plautii__Y18187.D.90.9 | 0.0840% | 0.0045% |
| SmartDNA0251.Alistipes__sp.SD16649 | 0.0883% | 0.0112% |
| SmartDNA0206.Flavobacterium__cauense.SD18252 | 1.6158% | 0.4843% |
| Alistipes__marseilloanorexicus | 0.0643% | 0.0090% |
| OTU122.NN.Oscillibacter__valericigenes__AB238598.D.90.9 | 0.0580% | 0.0035% |
| OTU1244.NN.Coprococcus__eutactus__EF031543.D.87.9 | 0.0131% | 0.0061% |
| SmartDNA0229..Eubacterium.siraeum.SD16609 | 1.4408% | 0.4113% |
| OTU914.NN.Ruminococcus__bromii__DQ882649.D.87.6 | 0.0246% | 0.0054% |

TABLE 17

Random Forest classification error rate for determining
whether a subject has IBS-C or IBS-D (species)

| Number of species used for classification | IBS-C | IBS-D | Overall |
|---|---|---|---|
| Top 100 | 0.0% | 6.0% | 3% |
| Top 50 | 2.0% | 8.0% | 5% |
| Top 30 | 2.0% | 8.0% | 5% |
| Top 15 | 6.0% | 8.0% | 7% |
| Top 5 | 10.0% | 10.0% | 10% |

TABLE 18

Top 50 most indicative bacterial species for determining
whether a subject has IBS-C or IBS-D (limma)

| Bacteria genus | Mean relative abundance Non-IBS | Mean relative abundance IBS |
|---|---|---|
| OTU662.NN.Papillibacter__cinnamivorans__AF167711.D.90.1 | 0.1874% | 0.0535% |
| OTU1682.NN.Oscillibacter__valericigenes__AB238598.D.91.1 | 0.7030% | 0.0535% |
| OTU131.NN.Oscillibacter__valericigenes__AB238598.D.93.5 | 0.3889% | 0.0740% |
| OTU480.NN.Butyrivibrio__crossotus__FR733670.D.85.8 | 0.0967% | 0.0069% |
| OTU1119.NN.Soleaferrea__massiliensis__JX101688.D.89.3 | 0.1189% | 0.0230% |
| Alistipes__obesi | 0.1394% | 0.0133% |
| OTU867.NN.Christensenella__minuta__AB490809.D.91.9 | 0.0484% | 0.0043% |
| OTU164.NN.Ruminococcus__bromii__DQ882649.D.85.6 | 0.0544% | 0.0134% |
| SmartDNA0136.Barnesiella__intestinihominis.NR__113073.SD17407 | 0.4300% | 0.0894% |
| OTU176.NN.Butyrivibrio__crossotus__FR733670.D.87.8 | 0.3139% | 0.0876% |
| OTU222.NN.Ruminococcus__bromii__DQ882649.D.89.9 | 0.1091% | 0.0173% |
| SmartDNA0207.Flavobacterium__resistens.SD18960 | 0.7398% | 0.2156% |
| OTU669.NN.Oscillospira.Flavonifractor._plautii__Y18187.D.88.2 | 0.0791% | 0.0292% |
| SmartDNA0206.Flavobacterium__cauense.SD18252 | 1.6158% | 0.4843% |
| OTU1700.NN.Clostridium__glycyrrhizinilyticum__AB233029.D.90.6 | 0.0311% | 0.2892% |
| SmartDNA0152.Anaerostipes__hadrus.SD18611 | 0.0135% | 0.1469% |
| OTU58.NN.Oscillospira.Flavonifractor._plautii__Y18187.D.95.5 | 0.1250% | 0.0409% |
| SmartDNA0187.Curtobacterium__pusillum.SD18704 | 0.9904% | 0.0533% |
| OTU918.NN.Oscillibacter__valericigenes__AB238598.D.88.4 | 0.9842% | 0.2545% |
| OTU962.NN.Oscillibacter__valericigenes__AB238598.D.89.7 | 0.2647% | 0.0152% |
| Prevotella__ruminicola | 0.0732% | 0.1273% |
| Blautia__wexlerae | 0.1449% | 0.3079% |
| OTU1176.NN.Anaerostipes__coli__JF412658.1.D.85.4 | 0.0404% | 0.2451% |
| OTU152.NN.Oscillibacter__valericigenes__AB238598.D.94.3 | 1.2829% | 0.0943% |
| Desulfitobacterium__frappieri | 0.0405% | 0.0086% |
| OTU331.NN.Blautia__coccoides__EF025906.D.93.2 | 0.0575% | 0.1648% |
| Akkermansia__muciniphila | 2.3882% | 0.1143% |
| OTU482.NN.Eubacterium__sulci__AJ006963.D.89.4 | 0.0536% | 0.0119% |
| OTU438.NN.Blautia__coccoides__EF025906.D.91.5 | 0.1059% | 0.2395% |
| OTU1501.NN.Blautia__wexlerae__EF036467.D.95.7 | 0.2313% | 0.4808% |
| OTU1349.NN.Blautia__wexlerae__EF036467.D.93.9 | 0.1045% | 0.2833% |
| OTU136.NN.Oscillospira.Pseudoflavonifractor._capillosus__AY136666.D.91.2 | 0.0620% | 0.0098% |
| OTU528.NN.Clostridium__symbiosum__CLORR16SAA.D.91.8 | 0.1944% | 0.4099% |
| OTU1343.NN.Eubacterium__rectale__AY804151.D.90.8 | 0.0159% | 0.0348% |
| SmartDNA0146.Bifidobacterium__bombi.SD18666 | 0.0595% | 0.4497% |
| OTU353.NN.Oscillibacter__valericigenes__AB238598.D.93.8 | 0.4395% | 0.1062% |
| OTU605.NN.Oscillibacter__valericigenes__AB238598.D.93.9 | 0.6123% | 0.0642% |
| OTU775.NN.Anoxystipes__fissicatena__NR__104800.1.D.93.3 | 0.2738% | 0.4838% |

TABLE 18-continued

Top 50 most indicative bacterial species for determining
whether a subject has IBS-C or IBS-D (limma)

| Bacteria genus | Mean relative abundance Non-IBS | Mean relative abundance IBS |
|---|---|---|
| OTU1315.NN.Eubacterium_desmolans_EUBRRDO.D.94.2 | 0.0560% | 0.2019% |
| OTU628.NN.Eubacterium_eligens_EUBRRDAA.D.92.4 | 0.1023% | 0.2214% |
| OTU428.NN.Christensenella_minuta_AB490809.D.84.9 | 0.0603% | 0.0013% |
| OTU739.NN.Clostridium_clostridioforme_AY169422.D.94.6 | 0.0674% | 0.1401% |
| OTU693.NN.Christensenella_minuta_AB490809.D.86.6 | 0.7557% | 0.0081% |
| Eubacterium_ramulus | 0.1300% | 0.3052% |
| OTU1425.NN.Eubacterium_rectale_AY804151.D.94.9 | 0.0718% | 0.1568% |
| OTU882.NN.Melainabacter_A1.D.94.7 | 0.0106% | 0.0197% |
| SmartDNA0251.Alistipes_sp.SD16649 | 0.0883% | 0.0112% |
| Alistipes_marseilloanorexicus | 0.0643% | 0.0090% |
| OTU776.NN.Oscillospira.Flavonifractor._plautii_Y18187.D.93.4 | 0.1284% | 0.0601% |
| OTU468.NN.Oscillospira.Flavonifractor._plautii_Y18187.D.93.9 | 0.0196% | 0.0032% |

TABLE 19

Limma classification error rate for determining
whether a subject has IBS-C or IBS-D (species)

| Number of species used for classification | IBS | Non-IBS | Overall |
|---|---|---|---|
| Top 100 | 2% | 4% | 3% |
| Top 50 | 2% | 6% | 4% |
| Top 30 | 6% | 6% | 6% |
| Top 15 | 6% | 4% | 5% |
| Top 5 | 6% | 6% | 6% |

There is a significant overlap between the species identified using the Random Forest and limma algorithms. From assessment of the results of both algorithms, the following bacterial species were identified as those whose abundance was most indicative of whether or not a subject with IBS had IBS-C or IBS-D: *Christensenella minuta, Soleaferrea massiliensis, Papillibacter cinnamivorans, Oscillibacter valericigenes, Ruminococcus bromii, Gemmiger formicilis, Desulfitobacterium frappieri, Alistipes obesi, Anaerofilum pentosovorans, Akkermansia muciniphila, Alkaliphilus crotonatoxidans, Eubacterium sulci, Bdellovibrio exovorus, Curtobacterium pusillum, Flavonifractor plautii, Ruminococcus lactaris, Mogibacterium neglectum, Roseburia inulinivorans, Butyricimonas virosa, Intestinimonas butyriciproducens, Butyrivibrio crossotus, Barnesiella intestinihominis, Flavobacterium resistens, Flavobacterium cauense, Clostridium glycyrrhizinilyticum, Anaerostipes hadrus, Prevotella ruminicola, Blautia wexlerae,* and *Anaerostipes coli.*

Tables 17 and 19 show that when only the top 5 species were used, the overall classification error rate was in the range of 6% to 10%, depending on the algorithm used. These results demonstrate that the abundance of as few as 5 species of bacteria can be used to successfully determine whether a subject with IBS has IBS-C or IBS-D, with an accuracy of approximately 90% to 94%. This accuracy increased to approximately 97% when the abundance of the top 100 species were used.

Example 10 Determining a Subtype of IBS in a Subject Who has been Diagnosed with IBS-M Similar methods to those described in Example 1 were used to identify potential species of bacteria whose abundance could be used to identify different subtypes within IBS-M (mixed). The IBS-M classification translates at the molecular level to an unstable, heterogeneous bacterial population whose molecular signature can be rapidly altered by the environment, food and other factors such as stress.

It was surprisingly found that it was possible to assign a subject, who had been diagnosed with IBS-M, as having constipation-dominant IBS-M (IBS-MC) or diarrhoea-dominant IBS-M (IBS-MD) based on the abundance of least 5 species of bacteria in a sample from the subject.

A Random Forest algorithm was used to identify the most indicative species of bacteria that could be used to distinguish between the newly determined IBS-MD and IBS-MC subtypes. The results are shown in Tables 20 and 21.

TABLE 20

Top 50 most indicative bacterial species for determining
whether a subject has IBS-MC or IBS-MD (Random Forest)

| Bacteria species name | Mean relative abundance IBS-MC | Mean relative abundance IBS-MD |
|---|---|---|
| SmartDNA0236.Peptoniphilus_coxii.SD18704 | 0.2805% | 0.0005% |
| OTU708.NN.Clostridium_clariflavum_NR_102987.1.D.78.5 | 0.3011% | 0.0030% |
| OTU1556.NN.Bacteroides_thetaiotaomicron_BNRRR16SB.D.95.9 | 0.0000% | 0.0222% |
| Bacteroides_coprocola | 0.0517% | 1.2627% |
| OTU1300.NN.Clostridium_clariflavum_NR_102987.1.D.78.2 | 0.1434% | 0.0000% |
| OTU1682.NN.Oscillibacter_valericigenes_AB238598.D.91.1 | 0.8105% | 0.0524% |
| SmartDNA0174.Clostridium_hveragerdense.SD18751 | 0.2541% | 0.0369% |
| Bacteroides_thetaiotaomicron | 0.0690% | 0.4154% |
| OTU1024.Ruminiclostridium_clariflavum.NR_102987 | 0.2619% | 0.0060% |
| OTU507.NN.Bacteroides_xylanisolvens_AB510713.D.97 | 0.1871% | 1.3459% |

TABLE 20-continued

Top 50 most indicative bacterial species for determining
whether a subject has IBS-MC or IBS-MD (Random Forest)

| Bacteria species name | Mean relative abundance IBS-MC | Mean relative abundance IBS-MD |
|---|---|---|
| OTU202.NN.Clostridium_clariflavum_NR_102987.1.D.78.7 | 0.1873% | 0.0000% |
| Clostridium_chauvoei | 0.0437% | 0.0039% |
| SmartDNA0181.Clostridium_tepidiprofundi.SD18704 | 0.3259% | 0.0594% |
| OTU925.NN.Papillibacter_cinnamivorans_AF167711.D.86.8 | 0.0294% | 0.0000% |
| SmartDNA0221.Lactococcus_fujiensis.SD18907 | 0.9212% | 0.1740% |
| OTU525.NN.Clostridium_clariflavum_NR_102987.1.D.78.1 | 0.2055% | 0.0000% |
| SmartDNA0004.Bacteroides_uniformis.SD16737 | 0.5825% | 1.8728% |
| OTU189.NN.Bacillus_thuringiensis_AM292029.D.79.1 | 0.0377% | 0.0000% |
| SmartDNA0214.Johnsonella_ignava.SD18734 | 0.2322% | 0.0110% |
| OTU918.NN.Oscillibacter_valericigenes_AB238598.D.88.4 | 1.1998% | 0.1482% |
| OTU136.NN.Oscillospira.Pseudoflavonifractor._capillosus_AY136666.D.91.2 | 0.0644% | 0.0078% |
| OTU152.NN.Oscillibacter_valericigenes_AB238598.D.94.3 | 1.1665% | 0.0710% |
| OTU962.NN.Oscillibacter_valericigenes_AB238598.D.89.7 | 0.3524% | 0.0008% |
| OTU428.NN.Christensenella_minuta_AB490809.D.84.9 | 0.0647% | 0.0011% |
| SmartDNA0200.Enterococcus_azikeevi.SD18929 | 0.2416% | 0.1162% |
| OTU131.NN.Oscillibacter_valericigenes_AB238598.D.93.5 | 0.3112% | 0.0981% |
| OTU944.NN.Intestinimonas_butyriciproducens_JX101685.1.D.91.5 | 0.0291% | 0.0079% |
| OTU482.NN.Eubacterium_sulci_AJ006963.D.89.4 | 0.0729% | 0.0269% |
| SmartDNA0207.Flavobacterium_resistens.SD18960 | 0.3337% | 0.6708% |
| OTU474.NN.Anaerotruncus_colihominis_DQ002932.D.89.2 | 0.0253% | 0.0090% |
| OTU353.NN.Oscillibacter_valericigenes_AB238598.D.93.8 | 0.5715% | 0.0892% |
| Bacteroides_fluxus | 0.0021% | 0.5478% |
| OTU1212.NN.Ruminococcus_lactaris_NR_027579.1.D.87.5 | 0.1818% | 0.0326% |
| OTU178.NN.Oscillibacter_valericigenes_AB238598.D.92.5 | 0.6930% | 0.4711% |
| OTU506.NN.Christensenella_minuta_AB490809.D.83.8 | 2.2312% | 0.3806% |
| OTU480.NN.Butyrivibrio_crossotus_FR733670.D.85.8 | 0.1269% | 0.0150% |
| OTU1508.NN.Eubacterium_rectale_AY804151.D.94.1 | 0.0527% | 0.4824% |
| Prevotella_ruminicola | 0.0806% | 0.1426% |
| OTU679.NN.Gemmiger_formicilis_GU562446.D.91.1 | 0.6857% | 0.1245% |
| OTU838.NN.Ruminococcus_flavefaciens_AY349157.D.96.4 | 0.0452% | 0.0008% |
| OTU333.NN.Faecalibacterium_prausnitzii_X85022.D.88.3 | 0.3763% | 0.0793% |
| OTU855.NN.Roseburia_faecis_AY804149.D.95.5 | 0.2642% | 0.0108% |
| SmartDNA0076.Lactobacillus_apis.SD18424 | 0.0309% | 0.0642% |
| OTU176.NN.Butyrivibrio_crossotus_FR733670.D.87.8 | 0.2610% | 0.1121% |
| OTU117.NN.Clostridium_bolteae_AJ508452.D.90.7 | 0.8900% | 0.0407% |
| OTU206.NN.Oscillibacter_valericigenes_AB238598.D.95.4 | 0.0000% | 0.0090% |
| OTU1357.NN.Roseburia_inulinivorans_AJ270474.D.93.9 | 0.1009% | 0.0273% |
| Blautia_wexlerae | 0.0842% | 0.2773% |
| SmartDNA0228.Oribacterium_sinus.SD18749 | 0.3880% | 0.1303% |
| SmartDNA0175.Clostridium_malenominatum.SD18708 | 0.2504% | 0.0205% |

TABLE 21

Classification error rate for determining whether
a subject has IBS-MC or IBS-MD (species)

| Number of species used for classification | IBS-MC | IBS-MD | Overall |
|---|---|---|---|
| Top 100 | 0.0% | 0.0% | 0.0% |
| Top 50 | 0.0% | 0.0% | 0.0% |
| Top 30 | 0.0% | 0.0% | 0.0% |
| Top 15 | 0.0% | 0.0% | 0.0% |
| Top 5 | 0.0% | 0.0% | 0.0% |

The following bacterial species were identified as those whose abundance was most indicative of whether or not a subject, who had been diagnosed with IBS-M, had IBS-MC or IBS-MD:

*Peptoniphilus coxii, Clostridium clariflavum, Bacteroides thetaiotaomicron, Bacteroides coprocola, Oscillibacter valericigenes, Clostridium hveragerdense, Ruminiclostridium clariflavum, Bacteroides xylanisolvens, Clostridium chauvoei, Clostridium tepidiprofundi, Papillibacter cinnamivorans, Lactococcus fujiensis, Bacteroides uniformis, Bacillus thuringiensis, Johnsonella ignava, Pseudoflavonifractor capillosus, Christensenella minuta, Enterococcus azikeevi, Intestinimonas butyriciproducens, Eubacterium sulci, Flavobacterium resistens, Anaerotruncus colihominis, Pseudoflavonifractor capillosus, Bacteroides fluxus, Ruminococcus lactaris, Butyrivibrio crossotus, Eubacterium rectale, Prevotella ruminicola, Gemmiger formicilis, Ruminococcus flavefaciens,* and *Faecalibacterium prausnitzii.*

Table 21 shows that, for the dataset used, when only the top 5 species were used the overall classification error rate was 0%. This demonstrates that the abundance of as few as 5 species of bacteria can be used to successfully determine whether a subject, who has been diagnosed with IBS-M, has IBS-MC or IBS-MD.

Example 11 Diagnosis of Autism in a Subject with IBS

The methods described in Example 1 were used to identify the species of bacteria whose abundance was most indicative of whether or not a subject with IBS had autism.

A Random forest algorithm was used to identify the most indicative species of bacteria, the results are shown in Table 22 and 23.

TABLE 22

Top 50 most indicative bacterial species for determining whether a subject with IBS has Autism

| Bacteria species name | Mean relative abundance Non-Autistic | Mean relative abundance Autistic |
|---|---|---|
| OTU1210.NN.Eubacterium__hallii__EUBRRDR.D.95.1 | 0.000783435 | 0.000198496 |
| OTU1343.NN.Eubacterium__rectale__AY804151.D.90.8 | 0.000559174 | 0.000170317 |
| Lachnobacterium__bovis | 0.000499719 | 0.000234149 |
| Lachnoclostridium__glycyrrhizinilyticum | 0.001030706 | 0.000553054 |
| OTU1201.NN.Blautia__glucerasea__AB588023.D.94.1 | 0.001769116 | 0.000775163 |
| OTU604.NN.Eubacterium__desmolans__EUBRRDO.D.93.8 | 0.004683656 | 0.001646697 |
| OTU439.NN.Eubacterium__hallii__EUBRRDR.D.97 | 0.001865504 | 0.000445413 |
| OTU120.NN.Anoxystipes__fissicatena__NR__104800.1.D.92.1 | 0.000574764 | 0.000358371 |
| OTU1049.NN.Eubacterium__hallii__EUBRRDR.D.95.9 | 0.000735138 | 0.000287947 |
| OTU1085.NN.Blautia__coccoides__EF025906.D.95.9 | 0.000923818 | 0.00030132 |
| Blautia__coccoides | 0.002011895 | 0.000925875 |
| OTU1307.NN.Faecalibacterium__prausnitzii__X85022.D.93.2 | 0.0026842 | 0.001120172 |
| OTU1197.NN.Eubacterium__hallii__EUBRRDR.D.96.5 | 0.000308594 | 2.96E-05 |
| OTU1193.NN.Clostridium__symbiosum__CLORR16SAA.D.93.4 | 0.001792908 | 0.001092788 |
| OTU1746.NN.Roseburia__inulinivorans__AJ270474.D.91.6 | 0.000449446 | 0.000211553 |
| OTU602.NN.Blautia__glucerasea__AB588023.D.93.2 | 0.001108251 | 0.000420169 |
| OTU920.NN.Anaerostipes__coli__JF412658.1.D.96.9 | 0.001533355 | 0.000685762 |
| OTU1115.NN.Coprococcus__comes__EF031542.D.95 | 0.000140798 | 1.91E-05 |
| OTU717.NN.Lachnospira__pectinoschiza__AY699278.D.87.7 | 0.003279809 | 0.00147718 |
| SmartDNA0133.Arthrobacter__creatinolyticus.SD16598 | 0.001013605 | 0.000610693 |
| OTU1159.NN.Clostridium__nexile__X73443.D.95.6 | 0.000772759 | 0.000942947 |
| OTU1008.NN.Faecalibacterium__prausnitzii__X85022.D.94.9 | 0.008631002 | 0.004947581 |
| Bifidobacterium__thermacidophilum | 0.000878449 | 0.000609019 |
| Anaerostipes__rhamnosus | 0.00052196 | 0.000259116 |
| OTU1274.NN.Clostridium__clariflavum__NR__102987.1.D.80.5 | 0.001744549 | 0.000633694 |
| OTU661.NN.Blautia__wexlerae__EF036467.D.94.9 | 0.001846819 | 0.000723338 |
| OTU1137.NN.Fusicatenibacter__saccharivorans__AB698912.D.94.7 | 0.001701325 | 0.001196125 |
| OTU1012.NN.Blautia__wexlerae__EF036467.D.92.8 | 0.001175369 | 0.000523412 |
| SmartDNA0123.Tolumonas__auensis.SD18946 | 0.000557168 | 0.000186498 |
| OTU563.NN.Anoxystipes__fissicatena__NR__104800.1.D.96.2 | 0.009031464 | 0.004944174 |
| OTU1028,NN.Ruminococcus__gnavus__JN713312.D.95.6 | 0.000663854 | 0.000352144 |
| SmartDNA0097.Peptococcus__niger.SD18174 | 0.002131209 | 0.002640534 |
| OTU829.NN.Eubacterium__rectale__AY804151.D.94.6 | 0.000679753 | 0.000273643 |
| OTU1424.NN.Dorea__formicigenerans__EUBRRDP.D.96.7 | 0.001622239 | 0.000730316 |
| Roseburia__intestinalis | 0.010938189 | 0.004904387 |
| OTU1501.NN.Blautia__wexlerae__EF036467.D.95.7 | 0.0049271 | 0.003472643 |
| OTU1048.NN.Clostridium__populeti__X71853.D.91.9 | 0.000699036 | 0.000373165 |
| OTU740.NN.Dorea__massiliensis__JX101687.D.94.4 | 0.001152166 | 0.000458396 |
| OTU628.NN.Eubacterium__eligens__EUBRRDAA.D.92.4 | 0.002459119 | 0.001414861 |
| SmartDNA0249.Pseudobutyrivibrio__xylanivorans.SD18698 | 0.017988701 | 0.011486248 |
| OTU1315.NN.Eubacterium__desmolans__EUBRRDO.D.94.2 | 0.002572297 | 0.000734254 |
| OTU1644.NN.Fusicatenibacter__saccharivorans__AB698912.D.94.3 | 0.000979688 | 0.000558141 |
| SmartDNA0076.Lactobacillus__apis.SD18424 | 0.000476765 | 0.000216095 |
| Lachnoclostridium__herbivorans | 0.000221346 | 4.99E-05 |
| Eubacterium__hallii | 0.00847434 | 0.002631403 |
| OTU1006.NN.Eubacterium__rectale__AY804151.D.93.3 | 0.001665232 | 0.001320036 |
| SmartDNA0080.Lactobacillus__gigeriorum.SD16655 | 0.00119348 | 0.00069355 |
| OTU1386.NN.Blautia__coccoides__EF025906.D.94 | 0.001073258 | 0.000520933 |
| OTU493.NN.Anoxystipes__fissicatena__NR__104800.1.D.92.4 | 0.004799928 | 0.002050625 |
| OTU537.NN.Fusicatenibacter__saccharivorans__AB698912.D.97 | 0.002073734 | 0.004456715 |

TABLE 23

Classification error rate for determining whether a subject with IBS has Autism

| Number of species used for classification | Autistic | Non-Autistic | Overall |
|---|---|---|---|
| Top 100 | 8.7% | 5.0% | 7.0% |
| Top 50 | 8.7% | 7.5% | 8.1% |
| Top 30 | 10.9% | 10.0% | 10.5% |
| Top 15 | 13.0% | 7.5% | 10.5% |
| Top 5 | 15.2% | 10.0% | 12.8% |

From assessment of the results, the following bacterial species were identified as those whose abundance was most indicative of whether or not a subject with IBS had Autism: *Eubacterium hallii, Eubacterium rectale, Lachnobacterium bovis, Lachnoclostridium glycyrrhizinilyticum, Blautia glucerasea, Eubacterium desmolans, Anoxystipes fissicatena, Blautia coccoides, Faecalibacterium prausnitzii, Clostridium symbiosum, Roseburia inulinivorans, Anaerostipes coli, Coprococcus comes, Lachnospira pectinoschiza, Arthrobacter creatinolyticus, Clostridium nexile, Bifidobacterium thermacidophilum, Anaerostipes rhamnosus, Clostridium clariflavum, Blautia wexlerae, Fusicatenibacter saccharivorans, Tolumonas auensis, Ruminococcus gnavus, Peptococcus niger, Dorea formicigenerans, Roseburia intestinalis, Blautia wexlerae, Clostridium populeti, Dorea massiliensis,* and *Eubacterium eligens.*

Table 23 shows that when only the top 5 species were used, the overall classification error rate was 12.8%, depending on the algorithm used. These results demonstrate that the abundance of as few as 5 species of bacteria can be used to diagnose Autism in a subject with IBS, with an accuracy of approximately 87%. This accuracy increased to approximately 93% when the abundance of the top 100 species were used.

Example 12 Monitoring the Effectiveness of a Treatment of a Dysbiosis

The methods described in Example 1 were used to monitor the effectiveness of treatment of IBS with a probiotic. Individuals were assigned to one of the four following groups at different stages throughout treatment: Non-BS (i.e., normal), IBS-C, IBS-D, or IBS-M. The individuals were subjected to two successive treatments with the probiotic and the abundance of bacteria in their microbiome profile was analysed to assign each individual to one of the four groups above. The results are shown in Table 24 below.

TABLE 24

Classification of individuals treated with a probiotic

| Class | Before treatment | After treatment 1 | After treatment 2 |
|---|---|---|---|
| Non-IBS | 7 | 25 | 43 |
| IBS-C | 7 | 5 | 1 |
| IBS-D | 47 | 21 | 4 |
| IBS-M | 0 | 0 | 0 |

Table 24 shows that there was a highly significant and progressive increase in the number of individuals classified as "Non-IBS" with each of the two successive probiotic treatments (Fisher's exact test p-value=$7.236e^{-16}$). The classification accuracy estimated for the model was above 85%. This accuracy was estimated by applying the model back to the reference (training) data which were treated as unknown samples.

Figure 3:
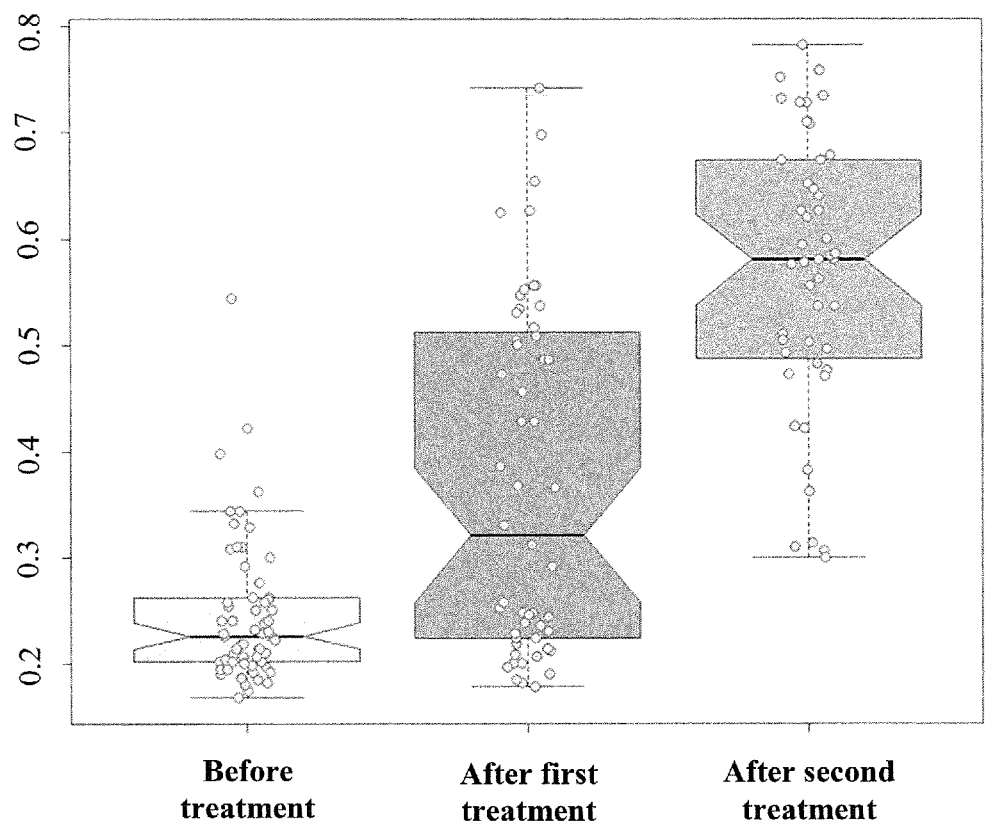
FIG. 3: Non-IBS classification score in subjects treated with a probiotic An overall classification score was assigned to each individual based on the probability of assigning that individual to the "Non-IBS" group. The score ranges from 0 to 1. A higher score corresponds to a more "Non-BS-like" microbiome. This figure shows that there was a significant and progressive increase in the average "Non-IBS" score across all individuals with each successive probiotic treatment.

The methods can also provide an overall classification score for each individual. This score could be treated as a probability of assigning an individual to a particular group. The score ranges from 0 to 1. A higher score corresponds to a better profile match to that particular training group. The sum of classification scores across the groups for each sample is equal to 1. FIG. 3 shows that there was a significant and progressive increase in the average "Non-IBS" score across all individuals with each successive probiotic treatment. This means that, on average, the individuals in the study were progressively becoming more "Non-IBS-like" (i.e., more "normal") as treatment with the probiotic progressed.

Example 13 Diagnosis of a Dysbiosis Associated with Intestinal Senescence

Similar methods to those described in Example 6 were used determine the species of bacteria that varied amongst subjects of different ages. Subjects were split into six different age categories, namely, A01: 2-5 y.o., A02: 5-10 y.o., A03: 10-20 y.o., A04: 20-40 y.o., A05: 40-60 y.o., and A06: 60-75 y.o. The subject's microbiome profiles were then used to train a Random Forest algorithm, which was in turn used to classify unknown samples into one of the six age categories.

The species of bacteria whose abundance varied most across the different age groups are listed in Table 25 below.

TABLE 25

Top 50 most indicative bacterial species for determining intestinal senescence
Bacteria species name SmartDNA0249.Pseudobutyrivibrio_xylanivorans.SD18698
Dorea_massiliensis
OTU728.NN.Blautia_glucerasea_AB588023.D.96.4
Lachnoclostridium_herbivorans
OTU1008.NN.Faecalibacterium_prausnitzii_X85022.D.94.9
OTU414.NN.Faecalibacterium_prausnitzii_X85022.D.96.7
Romboutsia_lituseburense
OTU1370.NN.Blautia_glucerasea_AB588023.D.94.8
OTU1729.NN.Faecalibacterium_prausnitzii_X85022.D.96
SmartDNA0238.Peptoniphilus_methioninivorax.SD18972
OTU1150.NN.Faecalibacterium_prausnitzii_X85022D.95.6
OTU78.NN.Faecalibacterium_prausnitzii_X85022D.96.5
OTU1404.NN.Faecalibacterium_prausnitzii_X85022D.91.5
OTU994.NN.Faecalibacterium_prausnitzii_X85022D.95.3
OTU1085.NN.Blautia_coccoides_EF025906D.95.9
OTU373.NN.Blautia_glucerasea_AB588023D.92.4
SmartDNA0225.Megamonas_funiformis.SD18906
OTU935.NN.Eubacterium_rectale_AY804151D.96.3
Clostridium_bifermentans
OTU1731.NN.Roseburia_intestinalis_AB661435D.97
OTU1048.NN.Clostridium_populeti_X71853D.91.9
Clostridium_hiranonis
OTU741.NN.Blautia_glucerasea_AB588023D.94.1
OTU1253.NN.Faecalibacterium_prausnitzii_X85022D.96.7
OTU471.NN.Romboutsia_lituseburense_CLORR16SCD.96.6
Peptoclostridium_difficile
OTU1068.NN.Lactonifactor_longoviformis_NR_043551.1.D.92.6
SmartDNA0168.Clostridium_caliptrosporum.SD18737
OTU1169.NN.Faecalibacterium_prausnitzii_X85022.D.95.4
Asaccharospora_irregulare
SmartDNA0175.Clostridium_malenominatum.SD18708
OTU829.NN.Eubacterium_rectale_AY804151.D.94.6
OTU333.NN.Faecalibacterium_prausnitzii_X85022.D.88.3
OTU528.NN.Clostridium_symbiosum_CLORR16SAA.D.91.8
Blautia_glucerasea
SmartDNA0182.Clostridium_thermoalcaliphilum.SD18680
Lachnoclostridium_glycyrrhizinilyticum
OTU1350.NN.Blautia_glucerasea_AB588023.D.96.6
OTU985.NN.Ruminococcus_faecis_FJ611794.2.D.94.9

TABLE 25-continued

Top 50 most indicative bacterial species for determining intestinal senescence
Bacteria species name OTU1307.NN.Faecalibacterium__prausnitzii__X85022.D.93.2
SmartDNA0151.Blautia__schinkii.SD18921
OTU1555.NN.Blautia__glucerasea__AB588023.D.95.4
OTU136.NN.Oscillospira.Pseudoflavonifractor.__capillosus__AY136666.D.91.2
Faecalibacterium__prausnitzii
OTU61.NN.Ruminococcus__faecis__FJ611794.2.D.96.8
SmartDNA0170.Clostridium__chromoreductans.SD18154
Clostridium__ghonii
OTU1092.NN.Clostridium__innocuum__CLOIRGNA.D.96.3
OTU813.NN.Faecalibacterium__prausnitzii__X85022.D.95.5
OTU1196.NN.Christensenella__minuta__AB490809.D.86.5

Using the species identified above, the Random Forest algorithm was able to correctly classify unknown subjects into one of the six age categories described above with an overall accuracy of 75%. This accuracy was further increased to 95% using a Support Vector Machine (SVM).

The species of bacteria identified are useful as markers for diagnosing a dysbiosis which is associated with age, for example intestinal senescence. From an assessment of the results, the following bacterial species were identified as those whose abundance was most indicative of a subject's age:

*Pseudobutyrivibrio xylanivorans, Dorea massiliensis, Blautia glucerasea, Lachnoclostridium herbivorans, Faecalibacterium prausnitzii, Romboutsia lituseburense, Peptoniphilus methioninivorax, Blautia coccoides, Megamonas funiformis, Eubacterium rectale, Clostridium bifermentans, Roseburia intestinalis, Clostridium populeti, Clostridium hiranonis, Peptoclostridium difficile, Lactonifactor longoviformis, Clostridium caliptrosporum, Asaccharospora irregulare, Clostridium malenominatum, Clostridium symbiosum, Clostridium thermoalcaliphilum, Lachnoclostridium glycyrrhizinilyticum, Ruminococcus faecis, Blautia schinkii, Pseudoflavonifractor capillosus, Clostridium chromoreductans, Clostridium ghonii, Clostridium innocuum, Christensenella minuta, Dorea formicigenerans,* and *Clostridium tertium.*

BIBLIOGRAPHY

Barber, D. (2012) *Bayesian Reasoning and Machine Learning.* Cambridge University Press, New York, N.Y., USA.
Berger & Kimmel, (1987) *Guide to Molecular Cloning Techniques.* Methods in Enzymology, Volume 152, Academic Press Inc., San Diego, Calif.
Caruana & Niculescu-Mizil, (2006) *An Empirical Comparison of Supervised Learning Algorithms.* Proceedings of the 23 rd International Conference on Machine Learning, Pittsburgh, Pa.
Cole et al., (2008) Nucleic Acids Research. Vol 35-Database issue: D169-Dl 72
Colowick, S. and Kaplan, N. (1963) *Methods In Enzymology* eds., Academic Press, Inc., whole of series.
Durbin et al., (1998) *Biological Sequence Analysis: Probabilistic Models of Proteins and Nucleic Acids.* Cambridge University Press.
Feng & Doolittle, (1987) *Progressive sequence alignment as a prerequisiteto correct phylogenetic trees.* J. Mol. Evolution., 25, 351-360.
Gait, M. J. (1984) *Oligonucleotide Synthesis: A Practical Approach.* IRL Press, Oxford. Particularly the papers therein by Gait, pp 1-22; Atkinson et al, pp 35-81; Sproat et al, pp 83-115; and Wu et al, pp 135-151; 4.
Gibas & Jambeck (2001) *Bioinformatics Computer Skills.* O'Reilly.
Glover, D. N. (1985) *DNA Cloning: A Practical Approach, Vols. I and II and III.* IRL Press, Oxford.
Hames, B. D. & Higgins, S. J. (1985) *Nucleic Acid Hybridization: A Practical Approach.* IRL Press, Oxford.
Higgins, H. G. & Sharp, P. M. (1989) *Fast and sensitive multiple sequence alignments on a microcomputer.* CABIOS, 5:151-153.
Hinchliffe (1996) *Modelling Molecular Structures.* John Wiley and Sons.
Ho, T. K. (1995) *Random Decision Forests.* Proceedings of the 3rd International Conference on Document Analysis and Recognition, Montreal, QC, 14-16 Aug. 1995 pp 278-282.
McPherson & Moller, (2006) *PCR, second edition.* Taylor & Francis Group.
Needleman, S. B. & Wunsch C. D., (1970) *A general method applicable to the search for similarities in the amino acid sequence of two proteins.* J. Mol. Biol. 48; 443-453.
Ondov, B. D. et al., (2011) *Interactive metagenomic visualization in a Web browser.* BMC Bioinformatics. 12:385. doi: 10.1186/1471-2105-12-385.
Perbal, B., (1984) *A Practical Guide to Molecular Cloning.*
Pevzner, (2000) *Computational Molecular Biology and Algorithmic Approach.* The MIT Press.
Pruesse et al., (2007) Nucleic Acid Research. Vol 35, p 7188.
Rashidi & Buehler, (2000) *Bioinformatic Basics: Applications in Biological Science and Medicine.* CRC Press LLC.
Rasmussen, C. E. & Williams, C. K. I. (2005) *Gaussian Processes for Machine Learning.* The MIT Press.
Ritchie et al., (2015) *limma powers differential expression analyses for RNA-sequencing and microarray studies.* Nucleic Acids Research.
Roig, M. G. (1985) *Immobilized Cells and Enzymes: A Practical Approach.* IRL Press, Oxford.
Sambrook, J., & Green, M. R. (2012). *Molecular Cloning: A Laboratory Manual (Fourth Edition).* New York: Cold Spring Harbour Laboratory Press.
Thijssen, P., (1993) *Hybridization with Nucleic Acid Probes.* Laboratory Techniques in Biochemistry and Molecular Biology, Vol. 24, Elsevier, N.Y.
Wiedman et al., (1994) PCR Meth Appl; 3:S51-S64.
Young & Davis, (1983) Proc. Natl. Acad. Sci. (USA) 80: 1194.

The invention claimed is:
1. A method of diagnosing and treating a dysbiosis in a human subject, comprising measuring an abundance of at least 5 species of bacteria in a sample from the subject and at least 5 species of bacteria in a sample derived from a reference population, wherein the at least 5 species of bacteria include *Corynebacterium minutissimum, Prevotella oulora, Fusobacterium naviforme, Prevotella ruminicola*, and *Bifidobacterium thermacidophilum*, and wherein a diagnosis of is made when the abundance of one or more species of bacteria differs in abundance between the sample from the human subject and the sample derived from the reference population; and treating the subject for dysbiosis by administering to the subject a composition to the subject which increases and/or decreases the abundance of the one or more species of bacteria that differs in abundance between the sample from the human subject and the sample derived from the reference population.

2. The method of claim 1, wherein the dysbiosis is IBS.

3. The method of claim 1, wherein the composition is a nutraceutical.

4. The method of claim 1, wherein the composition is a probiotic.

5. The method of claim 1, wherein the composition is a faecal microbiota transplant.

6. The method of claim 1, wherein the subject has previously been administered a chemotherapy or an antibiotic.

7. The method of claim 1, wherein the sample is a faecal sample.

8. The method of claim 1, further comprising measuring the abundance of at least one species of bacteria selected from *Dysgonomonas wimpennyi, Propionibacterium acnes, Corynebacterium tuberculostearicum, Brevibacterium casei, Lachnobacterium bovis, Prevotella dentasini, Prevotella albensis, Veillonella atypica, Kytococcus schroeteri, Prevotella copri, Bacteroides barnesiae, Prevotella conceptionensis, Anaerofustis stercorihominis, Bifidobacterium thermophilum, Prevotella brevis, Roseburia intestinalis, Clostridium symbiosum, Barnesiella intestinihominis, Bacteroides fragilis, Anaerostipes rhamnosus, Collinsella aerofaciens, Clostridium bolteae, Arthrobacter creatinolyticus, Atopobium fossor, Prevotella paludivivens*, and *Pelotomaculum isophthalicicum*.

9. A method of diagnosing and treating a dysbiosis in a human subject, comprising measuring an abundance of at least one species of each of 5 genera of bacteria in a sample from the subject and at least one species of each of 5 genera of bacteria in a sample derived from a reference population, wherein the at least 5 genera of bacteria include *Corynebacterium, Lachnobacterium, Propionibacterium, Kytococcus*, and *Fusobacterium*, and wherein a diagnosis of dysbiosis is made when the abundance of one or more genera of bacteria differs in abundance between the sample from the human subject and the sample derived from the reference population; and treating the subject for dysbiosis by administering to the subject a composition which increases and/or decreases the abundance of the at least one species of the one or more genera of bacteria in the subject, thereby treating the subject.

10. The method of claim 9, wherein the dysbiosis is IBS.

11. The method of claim 9, further comprising measuring the abundance of at least one species of at least one genus of bacteria selected from *Veillonella, Prevotella, Anaerofustis, Arthrobacter, Dysgonomonas, Calothrix, Atopobium, Brevibacterium, Micrococcus, Burkholderia, Veillonella, Pelotomaculum, Acidaminococcus, Mitsuokella, Allisonella, Odoribacter, Bacteroides, Coprobacter, Alistipes, Ruminococcus, Ferrimonas, Alkaliphilus*, and *Lautropia*.

12. A method of determining a subtype of IBS in a human subject with IBS and treating the subject, comprising a) measuring an abundance of at least 5 species of bacteria in a sample from the subject, wherein the at least 5 species of bacteria include *Christensenella minuta, Soleaferrea massiliensis, Papillibacter cinnamivorans, Oscillibacter valericigenes*, and *Ruminococcus bromii* and comparing the abundance of the at least 5 species of bacteria in the sample from the human subject to the abundance of the at least 5 species of bacteria in a sample derived from a reference population thereby determining a subtype of IBS; and b) administering a composition to the subject which increases and/or decreases the abundance of one or more species of bacteria in the subject, thereby treating the subject.

13. The method of claim 12, further comprising measuring the abundance of at least one species of bacteria selected from *Gemmiger formicilis, Desulfitobacterium frappieri, Alistipes obesi, Anaerofilum pentosovorans, Akkermansia muciniphila, Alkaliphilus crotonatoxidans, Eubacterium sulci, Bdellovibrio exovorus, Curtobacterium pusillum, Flavonifractor plautii, Ruminococcus lactaris, Mogibacterium neglectum, Roseburia inulinivorans, Butyricimonas virosa, Intestinimonas butyriciproducens, Butyrivibrio crossotus, Barnesiella intestinihominis, Flavobacterium resistens, Flavobacterium cauense, Clostridium glycyrrhizinilyticum, Anaerostipes hadrus, Prevotella ruminicola, Blautia wexlerae*, and *Anaerostipes coli*.

\* \* \* \* \*